(12) United States Patent
Prlic et al.

(10) Patent No.: US 12,152,252 B2
(45) Date of Patent: Nov. 26, 2024

(54) SYSTEMS AND METHODS FOR IMMUNOMODULATION OF MUCOSAL-ASSOCIATED INVARIANT T CELLS

(71) Applicant: Fred Hutchinson Cancer Center, Seattle, WA (US)

(72) Inventors: Martin Prlic, Seattle, WA (US); Julia Berkson, Seattle, WA (US); Chloe Slichter, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 1240 days.

(21) Appl. No.: 16/480,273

(22) PCT Filed: Jan. 23, 2018

(86) PCT No.: PCT/US2018/014878
§ 371 (c)(1),
(2) Date: Jul. 23, 2019

(87) PCT Pub. No.: WO2018/136948
PCT Pub. Date: Jul. 26, 2018

(65) Prior Publication Data
US 2019/0382725 A1  Dec. 19, 2019

Related U.S. Application Data

(60) Provisional application No. 62/449,494, filed on Jan. 23, 2017.

(51) Int. Cl.
| | |
|---|---|
| C12Q 1/68 | (2018.01) |
| C12N 5/0783 | (2010.01) |
| C12Q 1/6876 | (2018.01) |
| G01N 33/68 | (2006.01) |

(52) U.S. Cl.
CPC ......... C12N 5/0638 (2013.01); C12Q 1/6876 (2013.01); G01N 33/68 (2013.01); C12N 2500/30 (2013.01); C12N 2501/2312 (2013.01); C12N 2501/2315 (2013.01); C12N 2501/2318 (2013.01); C12N 2501/50 (2013.01); C12N 2501/998 (2013.01); C12Q 2600/158 (2013.01)

(58) Field of Classification Search
None
See application file for complete search history.

(56) References Cited

PUBLICATIONS

Sattler (European Journal of Immunology, 2015, vol. 45, pp. 2286-2298). (Year: 2015).*
Wilgenburg et al. 2016 Nature communications Supplemental data (Year: 2016).*
Barathan, et al., "Peripheral loss of CD8+CD161++TCRVa7.2+ mucosal-associated invariant T cells in chronic hepatitis C virus-infected patients," Eur. J. Clin. Invest., vol. 46, No. 2, 2016, pp. 170-180.
Liuzzi, "Unconventional T-cell driven inflammatory responses during acute peritonitis: implications for diagnosis and therapy of peritoneal dialysis patients," 2016 Cardiff University retrieved on May 1, 2018 at <<http://orca.cf.ac.uk/93396/1/2016LiuzziAnnaRitaPhD%20pdf.pdf>>286 pages.
Invitation to Pay Additional Fees Dated Mar. 23, 2018 for International Application No. PCT/US18/14878, 3 pages.
Search Report and Written Opinion Dated May 18, 2018 for International Application No. PCT/US18/14878, 20 pages.
Van Wilgenburg, et. al., "MAIT cells are activated during human viral infections," Nat. Commun., vol. 7, 2016, 11653, pp. 1-11.
Wong, et. al., "The role of mucosal-associated invariant T cells in infectious diseases," Immunology, vol. 150, 2016, pp. 45-54.
Anders, et al., "HTSeq-a Python framework to work with high-throughput sequencing data," Bioinformatics, vol. 31, No. 2, 2015, pp. 166-169.
Dias, et al., "Human MAIT-cell responses to *Escherichia coli*: activation, cytokine production, proliferation, and cytotoxicity," J. Leukoc. Biol., vol. 100, No. 1, 2016, pp. 233-240.
Huang, et al., "Evidence for MR1 antigen presentation to mucosal-associated invariant T cells," J. Biol. Chem., vol. 280, No. 22, 2005, pp. 21183-2193.
Langmead, et al., "Ultrafast and memory-efficient alignment of short DNA sequences to the human genome," Genome Biol., vol. 10, 2009, 10 pages.
Law, et al., "voom: Precision weights unlock linear model analysis tools for RNA-seq read counts," Genome Biol., vol. 15, No. 2, 2014, R29, 17 pages.
Liu, et al., "Why weight? Modelling sample and observational level variability improves power in RNA-seq analyses," Nucleic Acids Res., vol. 43, No. 15, 2015, e97, 11 pages.
Ritchie, et al., "limma powers differential expression analyses for RNA-sequencing and microarray studies," Nucleic Acids Res., vol. 43, No. 7, 2015, e47, 13 pages.
Robinson and Ashlack, "A scaling normalization method for differential expression analysis of RNA-seq data," Genome Biol., vol. 11, No. 3, 2010, R25, 9 pages.
Slichter, et al., "Distinct activation thresholds of human conventional and innate-like memory T cells," JCI Insight., vol. 1, No. 8, 2016, pii: e86292, 16 pages.
Trapnell and Schatz, "Optimizing Data Intensive GPGPU Computations for DNA Sequence Alignment," Parallel Comput., vol. 35, No. 8, 2009, pp. 429-440.

(Continued)

Primary Examiner — Celine X Qian
(74) Attorney, Agent, or Firm — C. Rachal Winger; Chrystal Quisenberry; Lee & Hayes PC

(57) ABSTRACT

Systems and methods to modulate the function of mucosal-associated invariant T (MAIT) cells in the absence of a T cell receptor (TCR) signal are described. The systems and methods can be used to elucidate the function of MAIT cells to assess potential therapeutic strategies for conditions associated with inflammation.

9 Claims, 9 Drawing Sheets
Specification includes a Sequence Listing.

(56) References Cited

PUBLICATIONS

Walker and Sansom, "Confusing signals: recent progress in CTLA-4 biology," Trends Immunol., vol. 36, No. 2, 2015, pp. 63-70.
Wong, et al.,"The role of mucosal-associated invariant T cells in infectious diseases," Immunology, vol. 150, No. 1, 2016, pp. 45-54.

* cited by examiner

1. Auto shut-off

2. Treg suppression

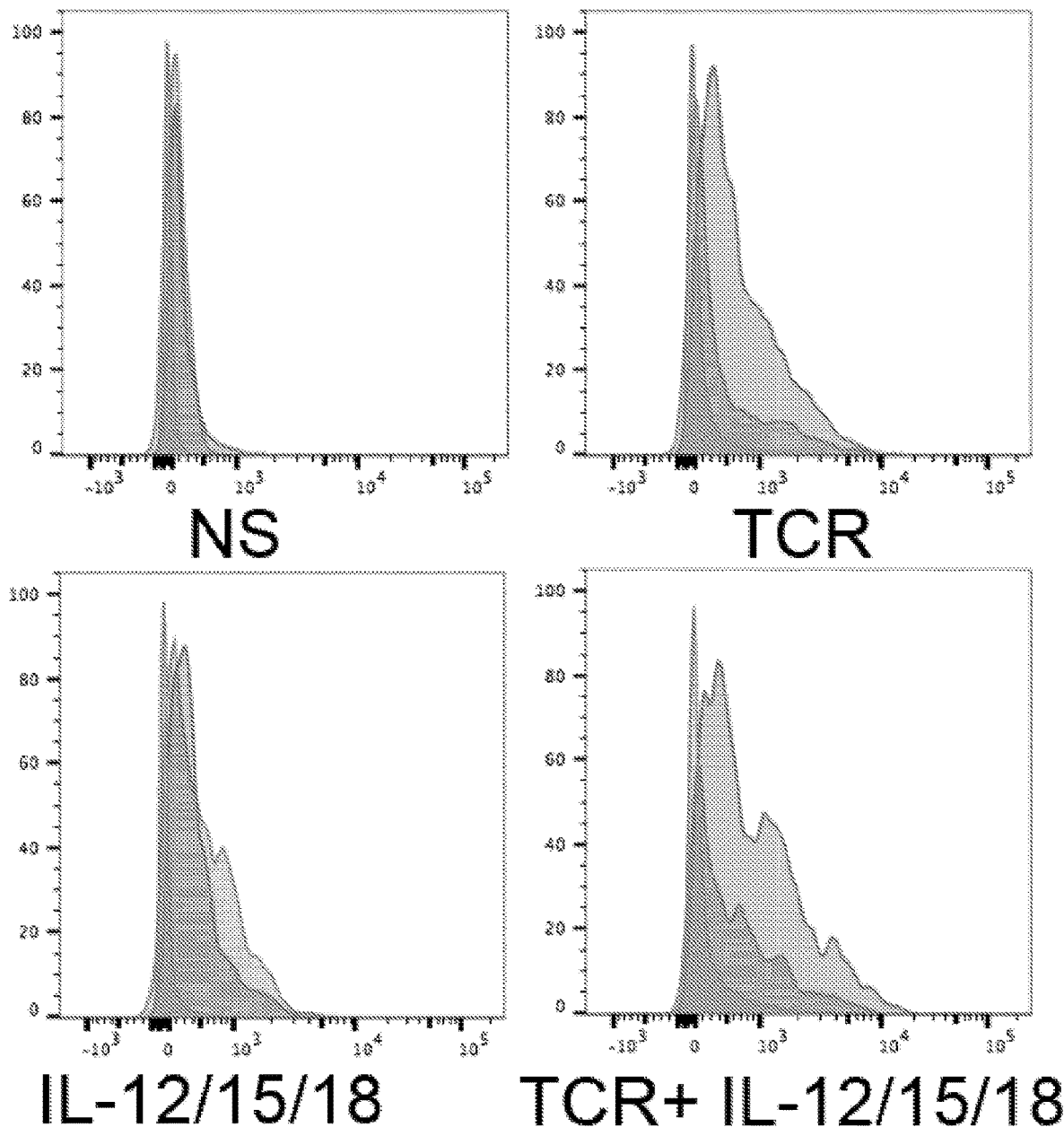

FIG. 6

>Homo sapiens IL-12 subunit alpha (UniProt Accession P29459)
MCPARSLLLVATLVLLDHLSLARNLPVATPDPGMFPCLHHSQNLLRAVSNMLQKARQTL
EFYPCTSEEIDHEDITKDKTSTVEACLPLELTKNESCLNSRETSFITNGSCLASRKTSFM
MALCLSSIYEDLKMYQVEFKTMNAKLLMDPKRQIFLDQNMLAVIDELMQALNFNSETVP
QKSSLEEPDFYKTKIKLCILLHAFRIRAVTIDRVMSYLNAS (SEQ ID NO: 1)

>Homo sapiens IL-12 subunit beta (UniProt Accession P29460)
MCHQQLVISWFSLVFLASPLVAIWELKKDVYVVELDWYPDAPGEMVVLTCDTPEEDGIT
WTLDQSSEVLGSGKTLTIQVKEFGDAGQYTCHKGGEVLSHSLLLLHKKEDGIWSTDIL
KDQKEPKNKTFLRCEAKNYSGRFTCWWLTTISTDLTFSVKSSRGSSDPQGVTCGAATL
SAERVRGDNKEYEYSVECQEDSACPAAEESLPIEVMVDAVHKLKYENYTSSFFIRDIIK
PDPPKNLQLKPLKNSRQVEVSWEYPDTWSTPHSYFSLTFCVQVQGKSKREKKDRVFT
DKTSATVICRKNASISVRAQDRYYSSSWSEWASVPCS (SEQ ID NO: 2)

>Pongo abelii IL-12 subunit alpha (UniProt Accession H2PBV7)
MWPPGSASQPPPSPAAATGLHPAARPVSLQCRLSMCPARSLLLVATLVLLDHLSLARN
LPVATPGPGMFPCLHHSQNLLRAVSNMLQKARQTLEFYPCTSEEIDHEDITKDQTSTV
EACLPLELTKNESCLNSRETSFITNGSCLASRKTSFMMALCLSSIYEDLKMYQVEFKTM
NAKLLMDPKRQIFLDQNMLAVIDELMQALNFNSETVPQKSSLEEPDFYKTKIKLCILLHA
FRIRAVTIDRVMNYLNAS (SEQ ID NO: 3)

>Pongo abelii IL-12 subunit beta (UniProt Accession H2PH86)
MCHQQLVISWFSLVFLASPLVAIWELKKDVYVVELDWYPDAPGEMVVLTCDTPEEDGIT
WTLDRSSEVLGSGKTLTIQVKEFGDAGQYTCHKGGEALSHSFLLLHKKEDGIWSTDIL
KDQKEPKNKTFLRCEAKNYSGRFTCWWLTTISTDLTFSVKSSRGSSDPQGVTCGAATL
SAERVRGDNKEYEYSVECQEDSACPAAEERLPIEVMVDAVHKLKYENYTSSFFIRDIIK
PDPPKNLQLKPLKNSRQVEVSWEYPDTWSTPHSYFSLTFCVQVQGKSKREKKDRVFT
DKTSATVICRKNANFSVRAQDRYYSSSWSEWASVPCS (SEQ ID NO: 4)

>Homo sapiens IL-15 isoform IL15-S48AA (UniProt Accession P40933-1)
MRISKPHLRSISIQCYLCLLLNSHFLTEAGIHVFILGCFSAGLPKTEANWVNVISDLKKIED
LIQSMHIDATLYTESDVHPSCKVTAMKCFLLELQVISLESGDASIHDTVENLIILANNSLSS
NGNVTESGCKECEELEEKNIKEFLQSFVHIVQMFINTS (SEQ ID NO: 5)

>Homo sapiens IL-15 isoform IL15-S21AA (UniProt Accession P40933-2)
MVLGTIDLCSCFSAGLPKTEANWVNVISDLKKIEDLIQSMHIDATLYTESDVHPSCKVTA
MKCFLLELQVISLESGDASIHDTVENLIILANNSLSSNGNVTESGCKECEELEEKNIKEFL
QSFVHIVQMFINTS (SEQ ID NO: 6)

>Mus musculus IL-15 (UniProt Accession P48346)
MKILKPYMRNTSISCYLCFLLNSHFLTEAGIHVFILGCVSVGLPKTEANWIDVRYDLEKIE
SLIQSIHIDTTLYTDSDFHPSCKVTAMNCFLLELQVILHEYSNMTLNETVRNVLYLANSTL
SSNKNVAESGCKECEELEEKTFTEFLQSFIRIVQMFINTS (SEQ ID NO: 7)

FIG. 6 CONT.

>Homo sapiens IL-18 isoform 1 (UniProt Accession Q14116-1)
MAAEPVEDNCINFVAMKFIDNTLYFIAEDDENLESDYFGKLESKLSVIRNLNDQVLF
IDQGNRPLFEDMTDSDCRDNAPRTIFIISMYKDSQPRGMAVTISVKCEKISTLSCE
NKIISFKEMNPPDNIKDTKSDIIFFQRSVPGHDNKMQFESSSYEGYFLACEKERDL
FKLILKKEDELGDRSIMFTVQNED (SEQ ID NO: 8)

>Homo sapiens IL-18 isoform 2 (UniProt Accession Q14116-2)
MAAEPVEDNCINFVAMKFIDNTLYFIENLESDYFGKLESKLSVIRNLNDQVLFIDQG
NRPLFEDMTDSDCRDNAPRTIFIISMYKDSQPRGMAVTISVKCEKISTLSCENKIISF
KEMNPPDNIKDTKSDIIFFQRSVPGHDNKMQFESSSYEGYFLACEKERDLFKLILK
KEDELGDRSIMFTVQNED (SEQ ID NO: 9)

>Mus musculus IL-18 (UniProt Accession P70380)
MAAMSEDSCVNFKEMMFIDNTLYFIPEENGDLESDNFGRLHCTTAVIRNINDQVLF
VDKRQPVFEDMTDIDQSASEPQTRLIIYMYKDSEVRGLAVTLSVKDSKMSTLSCK
NKIISFEEMDPPENIDDIQSDLIFFQKRVPGHNKMEFESSLYEGHFLACQKEDDAF
KLILKKKDENGDKSVMFTLTNLHQS (SEQ ID NO: 10)

SYSTEMS AND METHODS FOR IMMUNOMODULATION OF MUCOSAL-ASSOCIATED INVARIANT T CELLS

CROSS-REFERENCE TO RELATED APPLICATIONS

This application is a U.S. National Phase Patent Application based on PCT/US2018/014878, filed on Jan. 23, 2018, which claims priority to U.S. Provisional Patent Application No. 62/449,494 filed Jan. 23, 2017, the contents of each of which are incorporated by reference herein in their entireties.

REFERENCE TO SEQUENCE LISTING

The Sequence Listing associated with this application is provided in text format in lieu of a paper copy, and is hereby incorporated by reference into the specification. The name of the text file containing the Sequence Listing is 24S0641 ST25.txt. The text file is 19 KB, was created on Jul. 16, 2019, and is being submitted electronically via EFS-Web.

FIELD OF THE DISCLOSURE

The current disclosure provides systems and methods to modulate the function of mucosal-associated invariant T (MAIT) cells in the absence of a T cell receptor (TCR) signal. The systems and methods can be used to elucidate the function of MAIT cells and to assess potential therapeutic strategies for conditions associated with inflammation.

BACKGROUND OF THE DISCLOSURE

Inflammation has long been a well-known response to combat infection and tissue injury. Immune cells play an important role in the induction and resolution or persistence of inflammation. Innate immune system responses provide immediate defense against infection by pathogens, while adaptive immune system responses create immunological memory after an initial response to a specific pathogen. Immunological memory leads to an enhanced immune response to subsequent encounters with a previously-encountered pathogen. White blood cells are the workhorses of both of the innate and the adaptive immune systems.

T cells are a subtype of white blood cells that are distinguished from other white blood cells by the presence of a T cell receptor (TCR) on the cell surface. Conventional T cells have TCRs that are composed of $\alpha$ and $\beta$ chains that are highly variable in sequence from one T cell to another. This diversity of TCRs on T cells is an important component of the adaptive immune system. Upon pathogen infection, TCRs are responsible for recognizing parts of an invading pathogen or its metabolites presented by antigen presenting cells (APCs), and recognition leads to a series of pro-inflammatory events to destroy cells infected by the pathogen.

A pro-inflammatory response by a conventional T cell can be dampened by expression of inhibitory receptors on its cell surface. One of these inhibitory receptors, cytotoxic T-lymphocyte antigen 4 (CTLA-4), is usually expressed on the surface of a conventional T cell in response to a TCR signal and thus serves to control a pro-inflammatory response by a negative feedback mechanism. In a cell-autonomous manner, CTLA-4 expressed by an activated T cell can directly deliver an inhibitory signal to that T cell to downregulate the immune response. In a cell-non-autonomous fashion, CTLA-4 expressed by a regulatory T cell, a cell which has a role in regulating or suppressing other cells in the immune system, can inhibit the activation of other T cells.

Mucosal-associated invariant T (MAIT) cells are a class of innate-like T cells that belong to the family of unconventional T cells. Like conventional T cells, MAIT cells have TCRs, but the $\alpha$ and $\beta$ chains making up MAIT TCRs are not as variable as those of conventional T cell TCRs. MAIT cells represent the most abundant population of innate-like T cells within human beings, accounting for 1-10% of total T cells in peripheral blood.

It is recognized now that MAIT cells are crucial to fighting pathogen infection. Cells infected by pathogens activate MAIT cells by two pathways. Similar to other T cells, MAIT cells are activated via TCR-dependent signaling. Alternatively, or additionally, cytokines (small proteins important in cell signaling) produced by infected cells can activate MAIT cells through cytokine receptors (Wong E B et al. (2016) Immunology 150: 45-54). Upon activation, MAIT cells produce pro-inflammatory cytokines and other products that help to destroy pathogen-infected cells. It is not clear, however, how one activation pathway relates to the other and how each contributes overall to MAIT cell function.

MAIT cells are found in peripheral blood, the liver, and mucosal tissues such as the respiratory tract and the gastrointestinal tract. MAIT cell activity has been associated with a number of disease settings, including bacterial infections, and pro-inflammatory diseases such as multiple sclerosis, psoriasis, and inflammatory bowel diseases (IBD). Thus, this large innate-like T cell population is likely to have an important role in human health.

IBD particularly encompasses a number of intestinal auto-inflammatory diseases including Crohn's disease (CD) and ulcerative colitis (UC). The disease is believed to result from an exaggerated immune response of the host against gut microbiota, but the causes of the exaggerated immune response are not known. Compared to MAIT cells in the gut of healthy individuals, MAIT cells found in the gut of IBD patients are activated and have increased and different cytokine secretion profiles.

Although it is becoming increasingly clear that MAIT cells are important innate-like T cells that can potentially be used or targeted for therapeutic purposes, much remains to be understood about MAIT cell biology and its immuno-protective versus immunopathologic effects in humans. Underscoring the difficulty of elucidating MAIT cell function in humans is the lack of a good animal model, as MAIT cell numbers in laboratory mice are low. Although transgenic and congenic mice have been developed to express high levels of MAIT cells, there is a need for human model systems to support elucidating the full therapeutic potential of immunomodulation with these cells. As MAIT cells and CTLA-4 are key regulators in inflammation, understanding their relationship can lead to development of tools to study inflammation and therapeutics directed toward inflammatory conditions associated with infectious and non-infectious diseases, autoimmune disorders and cancer.

SUMMARY OF THE DISCLOSURE

The current disclosure provides systems and methods to further elucidate the role of mucosal-associated invariant T (MAIT) cells in a number of disease settings, including bacterial infections and pro-inflammatory conditions. Particular embodiments provide systems and methods to upregulate the inhibitory receptor cytotoxic T-lymphocyte antigen 4 (CTLA-4) on MAIT cells in the absence of a T cell receptor (TCR) signal. It was not previously known that CTLA-4 expression could be upregulated on MAIT cells in the absence of a TCR signal, so the current disclosure provides an important advance in the ability to elucidate the behavior and function of MAIT cells in a variety of pathologic conditions. In particular embodiments, systems and methods disclosed herein induce CTLA-4 expression utilizing general inflammatory conditions in the absence of a TCR signal. In particular embodiments, general inflammatory conditions include exposure to the cytokines interleukin (IL)-12, IL-15 and IL-18. In particular embodiments, exposure to general inflammatory conditions is short term exposure. As indicated, activating MAIT cells with general inflammatory conditions in the absence of a TCR signal and/or in the absence of infection can allow for the delineation of molecules and factors important in the role of MAIT cells in inflammation. In diseases associated with inflamed mucosal tissues, the ability to induce CTLA-4 expression on MAIT cells may reduce inflammation and pathology.

BRIEF DESCRIPTION OF FIGURES

Many of the drawings submitted herein are better understood in color. Applicants consider the color versions of the drawings as part of the original submission and reserve the right to present color images of the drawings in later proceedings.

FIG. 3A shows representative FACS histograms displaying expression levels of CTLA-4 in CD8$^+$ cells (CD3$^+$CD4$^-$CD8$^+$Vα7.2$^-$CD161$^-$), CD4$^+$ Treg cells (CD3$^+$CD4$^+$CD8$^-$CD25$^{hi}$IL-7rα$^{lo}$Foxp3$^+$Helios$^+$), and MAIT cells after no stimulation (NS), stimulation through TCR signal (TCR), stimulation with cytokines IL-12, IL-15, IL-18 (IL-12/15/18), and stimulation through both TCR signal and cytokines IL-12, IL-15, IL-18 (TCR+IL-12/15/18). The X-axis shows relative fluorescence as a measure of CTLA-4 expression and the Y-axis shows percentage of cells in the indicated cell population.

FIG. 5A, A representative flow plot of the CD161$^{hi}$CCR6$^{hi}$ MAIT cell population in the blood after gating on CD8$^+$ cells is shown (left panel). MAIT cell purity was confirmed after sorting CD8$^+$CD161$^{hi}$CCR6$^{hi}$CD62L$^{lo}$ cells by determining Vα7.2 expression in a small aliquot (right panel). FIG. 5B, Expression of granzyme B and IFNγ by CD8$^+$CD161$^{hi}$CCR6$^{hi}$CD62L$^{lo}$ sorted MAIT cells after 24 hours of rest (circles), anti-CD3/CD28 stimulation (squares), or 100 ng/ml IL-12/15/18 stimulation (triangles). FIG. 5C, 1,500-2,000 sorted CD8$^+$CD161$^{hi}$CCR6$^{hi}$CD62L$^{lo}$ cells were rested (circles), stimulated with anti-CD3/CD28 beads (squares), or stimulated with IL-12/15/18 (triangles) for 24 hours followed by analysis of the culture supernatants by Luminex. FIG. 5D, CD8$^+$CD161$^{hi}$CCR6$^{hi}$CD62L$^{lo}$ MAIT cells were stimulated with IL-12/15/18 in the presence (squares) or absence (triangles) of blocking anti-MR1 antibody (50 µg/ml), or rested (black circles). FIG. 5E, In parallel to the experiment described in FIG. 5D, CD8$^+$CD161$^{hi}$CCR6$^{hi}$CD62L$^{lo}$ MAIT cells were stimulated with monocytes that were incubated with paraformaldehyde-fixed *E. coli* to show efficacy of the blocking anti-MR1 antibody. MAIT cell activation was determined by induction of CD69$^+$CD25$^+$ expression. MAIT cell activation in the absence of blocking anti-MR1 antibody equals 100%. At least 3 different donors were used for each experiment shown.

FIG. 6 shows representative IL-12, IL-15, and IL-18 sequences (SEQ ID NOs: 1-10).

DETAILED DESCRIPTION

Inflammation has long been a well-known response to combat infection and tissue injury. Immune cells play an important role in the induction and resolution or persistence of inflammation. Innate immune system responses provide immediate defense against infection by pathogens, while adaptive immune system responses create immunological memory after an initial response to a specific pathogen. Immunological memory leads to an enhanced response to subsequent encounters with a previously-encountered pathogen. White blood cells are the workhorses of both of the innate and the adaptive immune systems.

T cells are a subtype of white blood cells that are distinguished from other white blood cells by the presence of a T cell receptor (TCR) on the cell surface. Conventional T cells have TCRs that are composed of α and β chains that are highly variable in sequence from one T cell to another. This diversity of TCRs on T cells is an important component of the adaptive immune system. Upon pathogen infection, TCRs are responsible for recognizing parts of an invading pathogen or its metabolites presented by antigen presenting cells (APCs), and recognition leads to a series of pro-inflammatory events to destroy cells infected by the pathogen.

Figure 1:
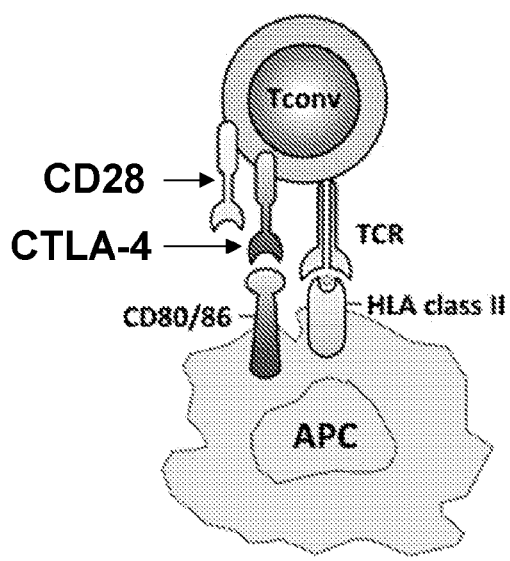
FIG. 1 shows a schematic of two ways that cytotoxic T-lymphocyte antigen 4 (CTLA-4) can downregulate an immune response. The activation of a conventional T cell relies on two signals: the first signal is provided by T cell receptor (TCR) binding to a ligand (e.g. part of a pathogen or a pathogen metabolite) presented by an antigen presenting cell (APC), and the second signal is provided by binding of costimulatory molecule CD28 on the T cell to integral membrane glycoproteins CD80 and CD86 present on the same APC. CTLA-4 expressed on the surface of an activated conventional T cell (CD4$^+$ and CD8$^+$) can bind to CD80/CD86 present on an APC, leading to a direct negative signal that inhibits the pro-inflammatory response of the activated T cell expressing CTLA-4 (auto shut-off). CTLA-4 expressed on the surface of a CD4$^+$ regulatory T cell (Treg) can suppress the activation of other T cells by competing with CD28 expressed on other T cells for binding to CD80 and CD86 on an APC (Treg suppression). Adapted from Walker LSK & Sansom D M (2015) Trends in immunology 36(2): 63-70.
Figure 1:
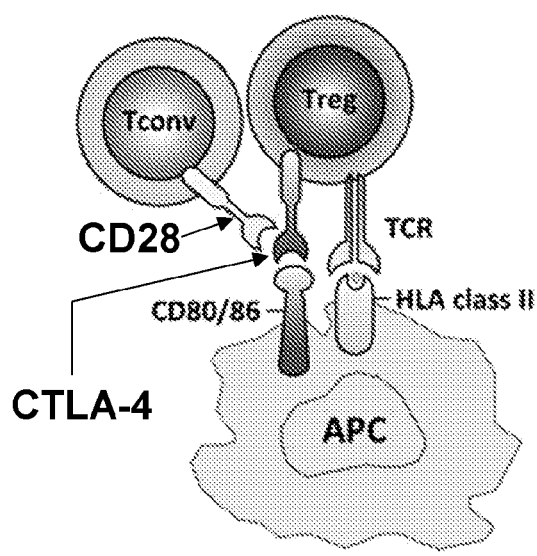

Referring to FIG. 1, the activation of a conventional T cell relies on two signals: the first signal is provided by TCR binding to a ligand (e.g. part of a pathogen or a pathogen metabolite) presented by an APC, and the second signal is provided by binding of costimulatory molecule CD28 on the T cell to integral membrane glycoproteins CD80 and CD86 present on the same APC. A pro-inflammatory response by a conventional T cell can be dampened by expression of inhibitory receptors on its cell surface. One of these inhibitory receptors, cytotoxic T-lymphocyte antigen 4 (CTLA-4), is usually expressed on the surface of a conventional T cell in response to a TCR signal and thus serves to control a pro-inflammatory response by a negative feedback mechanism. In a cell-autonomous manner, CTLA-4 expressed on the surface of an activated conventional T cell (CD4+ or CD8+) can bind to CD80/CD86 present on an APC, leading to a direct negative signal that inhibits the pro-inflammatory response of the activated T cell expressing CTLA-4 (auto shut-off). In a cell-non-autonomous fashion, CTLA-4 can inhibit the activation of other T cells by a competitive antagonism. In this mechanism, CTLA-4 expressed by a regulatory T cell, a cell which has a role in regulating or suppressing other cells in the immune system, competes with CD28 expressed on other T cells for binding to CD80 (B7-1) and CD86 (B7-2) on an APC (Treg suppression). The higher affinity of CTLA-4 compared to that of CD28 for CD80 or CD86 favors the formation of CTLA-4/CD80 or CTLA-4/CD86 inhibitory complexes over CD28/CD80 or CTLA-4/CD86 activating complexes.

Mucosal-associated invariant T (MAIT) cells are a class of innate-like T cells that belong to the family of unconventional T cells. Like conventional T cells, they have TCRs but the α and β chains making up MAIT TCRs are not as variable as those of conventional T cell TCRs. MAIT cells represent the most abundant population of innate-like T cells within human beings, accounting for 1-10% of total T cells in peripheral blood.

It is recognized now that MAIT cells are crucial to fighting pathogen infection. Cells infected by pathogens activate MAIT cells by two pathways. Similar to other T cells, MAIT cells are activated via TCR-dependent signaling. The TCR-dependent signaling involves binding of the MAIT cell TCR to vitamin B metabolites presented by a Major Histocompatibility Complex Class I (MHC)-like molecule, MR1, on APCs. Alternatively, or additionally, cytokines (small proteins important in cell signaling) produced by infected cells can activate MAIT cells through cytokine receptors (Wong E B et al. (2016) Immunology 150: 45-54). Upon activation, MAIT cells produce pro-inflammatory cytokines and other products that destroy pathogen-infected cells. It is not clear, however, how one pathway relates to the other and how each contributes overall to MAIT cell function.

MAIT cells are found in peripheral blood, the liver, and mucosal tissues such as the respiratory tract and the gastrointestinal tract. MAIT cell activation has been associated with a number of disease settings, including bacterial infections, and pro-inflammatory diseases such as multiple sclerosis, psoriasis, and inflammatory bowel diseases (IBD).

IBD particularly encompasses a number of intestinal auto-inflammatory diseases including Crohn's disease (CD) and ulcerative colitis (UC). The disease is believed to result from an exaggerated immune response of the host against gut microbiota, but the causes of the exaggerated immune response are unknown. Studies have shown that the frequency of MAIT cells are reduced in peripheral blood and accumulate in inflamed mucosa of the gut in individuals with IBD, although other studies have also shown that in individuals with IBD that included both CD and UC, the number of MAIT cells in the inflamed portion of the intestine was actually decreased. Compared to MAIT cells in the gut of healthy individuals, the MAIT cells found in the gut of IBD patients are activated and have increased and different cytokine secretion profiles.

Although it is becoming increasingly clear that MAIT cells are important innate-like T cells that can potentially be used or targeted for therapeutic purposes, much remains to be understood about MAIT cell biology and its immunoprotective versus immunopathologic effects in humans. Underscoring the difficulty of elucidating MAIT cell function in humans is the lack of a good animal model, as MAIT cell numbers in laboratory mice are low. Although transgenic and congenic mice have been developed to express high levels of MAIT cells, there is a need for human model systems to support elucidating the full therapeutic potential of immunomodulation with these cells. As MAIT cells and CTLA-4 are key regulators in inflammation, understanding their relationship can lead to development of tools to study inflammation and therapeutics directed toward inflammatory conditions associated with infectious and non-infectious diseases, autoimmune disorders and cancer.

The current disclosure provides systems and methods to further elucidate the role of MAIT cells in a number of disease settings, including bacterial infections and pro-inflammatory conditions. Particular embodiments provide systems and methods to upregulate the inhibitory receptor CTLA-4 on MAIT cells in the absence of a TCR signal and/or in the absence of infection. It was not previously known that CTLA-4 expression could be upregulated on MAIT cells in the absence of a TCR signal, so the current disclosure provides an important advance in the ability to elucidate the behavior and function of MAIT cells in a variety of pathologic conditions. In particular embodiments, systems and methods disclosed herein induce CTLA-4 expression utilizing general inflammatory conditions in the absence of a TCR signal. In particular embodiments, general inflammatory conditions include exposure to the cytokines interleukin (IL)-12, IL-15 and IL-18 or through exposure to cytokines that utilize common signaling pathways to IL-12, IL-15, and IL-18. In particular embodiments, exposure to general inflammatory conditions is short term exposure. As indicated, activating MAIT cells with general inflammatory conditions in the absence of a TCR signal and/or in the absence of infection can allow for the delineation of molecules and factors important in the role of MAIT cells in inflammation. In diseases associated with inflamed mucosal tissues, the ability to induce CTLA-4 expression on MAIT cells may reduce inflammation and pathology.

In particular embodiments, MAIT cell expression of CTLA-4 can be induced by (1) avoiding or inhibiting TCR signaling in MAIT cells, and (2) stimulating MAIT cells continuously with general inflammatory conditions for an effective duration of time. In particular embodiments, MAIT cell expression of CTLA-4 can be induced by (1) avoiding or inhibiting TCR signaling in MAIT cells, and (2) stimulating MAIT cells with general inflammatory conditions for a first effective duration of time, followed by rest in culture for a second effective duration of time. After stimulating MAIT cells with general inflammatory conditions for a first effective duration of time, the general inflammatory conditions can be removed, the MAIT cells can be washed with culture media, and the MAIT cells can be resuspended in culture media prior to returning the MAIT cells to an incubator for rest in culture for a second effective duration of time.

In particular embodiments, modulation of MAIT cell function by stimulation with general inflammatory conditions in the absence of a TCR signal leads to decreased activation of a MAIT cell as assessed by a reduction in CD69 and/or CD25 expression compared to a positive activated MAIT cell control. In particular embodiments, modulation of MAIT cell function by stimulation with general inflammatory conditions in the absence of a TCR signal leads to reduction in activation of a MAIT cell to 25% or less as compared to a positive activated MAIT cell control. In particular embodiments, modulation of MAIT cell function by stimulation with general inflammatory conditions in the absence of a TCR signal leads to a reduction in expression of CD69 and/or CD25 on a MAIT cell of 75% or more as compared to a positive activated MAIT cell control. In particular embodiments, modulation of MAIT cell function leads to a reduction in the percentage of MAIT cells within a MAIT cell population that secrete one or more cytokines, one or more cytolytic molecules, one or more chemokines, or a combination thereof. In particular embodiments, modulation of MAIT cell function leads to a reduction in secretion of one or more cytokines, one or more cytolytic molecules, one or more chemokines, or a combination thereof by individual MAIT cells within a MAIT cell population. In particular embodiments, the one or more cytokines include IFNγ, the one or more cytolytic molecules include granzyme B, and the one or more chemokines include CCL3. In particular embodiments, the percentage of MAIT cells that secrete granzyme B is reduced to 70% or less as compared to a positive activated MAIT cell control. In particular embodiments, the percentage of MAIT cells that secrete IFNγ is reduced to 70% or less as compared to a positive activated MAIT cell control. In particular embodiments, modulation of MAIT cell function leads to an induction of CTLA-4 expression on the surface of a MAIT cell in the absence of a TCR signal.

The following aspects of the disclosure are now described in additional detail: (i) cells and culture media; (ii) general inflammatory conditions; (iii) conditions for absence of a TCR signal in MAIT cells; (iv) methods to select for MAIT cells; (v) assays to measure CTLA-4 expression and MAIT cell modulation; and (vi) kits.

(i) Cells and Culture Media. Mononuclear cells, generally including monocytes and lymphocytes, can be obtained from, e.g., blood, peripheral blood, bone marrow, cord blood, mucosal tissue, gastrointestinal tract, liver, and lung. Mononuclear cells can be obtained by a known method such as centrifugation, magnetic beads and flow cytometry. Mononuclear cells can be those derived from stem cells such as induced pluripotent stem cells, embryonic stem cells and somatic stem cells. In particular embodiments, mononuclear cells can be obtained from mucosal tissue. In particular embodiments, peripheral blood mononuclear cells (PBMC) can be used as mononuclear cells in the present disclosure. PBMCs can be isolated by density gradient centrifugation with commonly used density gradient medium such as Ficoll or Ficoll-Paque. The density gradient medium can further include sodium diatrizoate, polysaccharides, and water. The PBMCs can be cryopreserved before using them in the methods of the present disclosure. Cryopreservation of PBMCs can include resuspension of the PBMCs in freezing medium. In particular embodiments, the freezing medium is 10-20% dimethyl sulfoxide (DMSO) and 40% fetal bovine serum (FBS) or human serum albumin (BSA) in RPMI-1640 medium. In particular embodiments, the PBMCs in freezing medium can be placed inside a freezing container at −80° C. overnight to allow gradual and even cooling. The frozen cells can be moved to a liquid nitrogen tank for long-term storage the following day. Cryopreserved PBMCs can be thawed to use in the methods of the present disclosure. In particular embodiments, thawing PBMCs include removing them from liquid nitrogen and placing them on ice, after which they are thawed in a 37° C. water bath. The thawing can further include: adding warm medium supplemented with 10% FBS, 1% penicillin/streptomycin, and L-glutamine, washing the cells to remove the DMSO, and resuspending the cells in medium. The thawing can further include resting the PBMCs overnight to remove any apoptotic cells. After this resting period, cells are washed, and are then ready to be used in culture.

A culture medium used in the present disclosure can include a nutrient component for enabling culture of mononuclear cells, a pH adjuster and the like. Examples include serum-free synthetic media for lymphocytes (such as KB550 and KB570), AIM-V, DC Medium, DMEM, RPMI-1640, X-VIVO™ culture medium and the like. Further, the form of a culture medium used in the present disclosure can be, for example, a mixture of components before preparation (a form of powder and the like), or those already prepared (a form of liquid and the like).

A culture medium used in the present disclosure can include a reagent commonly used in cell culture. Such reagents include antibiotics (gentamycin, kanamycin and the like), albumin, blood serum (human blood serum, FBS and the like), 2-mercaptoethanol, sodium pyruvate, growth factors such as insulin, L-glutamine, transferrin and the like. The culture medium can include proliferation agents such as phytohemagglutinin, lipopolysaccharide, and the like.

Conditions used for common cell culture may be used. For example, culturing may be performed at 30 to 38° C. and 5 to 10% $CO_2$.

In particular embodiments, culture media used in the present disclosure contains an effective amount of cytokines to create general inflammatory conditions as described below.

(ii) General Inflammatory Conditions. Cytokines are small proteins (5-20 kDa) that are important in cell signaling. Their release from cells has an effect on the behavior of cells around them. Cytokines can include chemokines, interferons (IFN), interleukins (IL), lymphokines, and tumor necrosis factors (TNF). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell.

Cytokines can be classified into four structural families: the four-α-helix bundle family including the IL-2, IFN and IL-10 subfamilies; the IL-1 family including IL-1 and IL-18; the IL-17 family, whose member cytokines have a specific effect in promoting proliferation of T-cells that cause cytotoxic effects; and the cysteine-knot family including members of the transforming-growth-factor-beta (TGF-β) superfamily, including TGF-β1, TGF-β2 and TGF-β3. Immunological cytokines can also be functionally classified into those that enhance cellular immune responses, type 1 (TNFα, IFN-γ, etc.), and those that favor antibody responses, type 2 (TGF-β, IL-4, IL-10, IL-13, etc.).

Cytokines act through receptors, and subsequent cascades of intracellular signaling that alter cell functions. In particular embodiments, cytokines are immunomodulating agents. Cytokines modulate the balance between humoral and cell-based immune responses, and they regulate the maturation, growth, and responsiveness of particular cell populations. Several inflammatory cytokines are induced by oxidative stress. Cytokines themselves trigger the release of other cytokines, which can also lead to increased oxidative stress. Thus, they are important in chronic inflammation, as well as in other immunoresponses, such as fever. Cytokines also play a role in anti-inflammatory pathways and are a possible therapeutic treatment for pathological pain from inflammation or peripheral nerve injury. There are both pro-inflammatory and anti-inflammatory cytokines that regulate this pathway.

Some cytokines enhance or inhibit the action of other cytokines in complex ways. They are important in health and disease, specifically in host responses to infection, immune responses, inflammation, trauma, sepsis, cancer, and reproduction.

IL-12 is naturally produced by dendritic cells, macrophages, neutrophils, and human B-lymphoblastoid cells in response to antigenic stimulation. It is a heterodimeric cytokine encoded by two separate genes, IL-12A (p35) and IL-12B (p40). The active heterodimer (p70) and a homodimer of p40 are formed following protein synthesis. It is known as a T cell-stimulating factor, promoting the growth and function of T cells. It stimulates the production of the cytokines IFN-γ and TNF-α from T cells and natural killer (NK) cells, cells which provide rapid responses to infection by pathogens.

IL-15 is structurally similar to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following infection by viruses. This cytokine induces cell proliferation of NK cells, cells of the innate immune system whose principal role is to kill virally infected cells.

IL-18 belongs to the IL-1 superfamily and is produced by macrophages and other cells. IL-18 works by binding to the IL-18 receptor, and together with IL-12 it induces cell-mediated immunity following infection with microbial products like lipopolysaccharide (LPS). After stimulation with IL-18, NK cells and certain T cells release IFN-γ or type II interferon that plays an important role in activating the macrophages or other cells.

In particular embodiments, any cytokine that signals through one or more signaling pathways that are used by IL-12, IL-15, and/or IL-18 can be used in the methods of the present disclosure. In particular embodiments, any cytokine that signals through a STAT4 (Signal Transducer and Activator of Transcription 4) and/or STAT5 signaling pathway can be used in the methods of the present disclosure.

IL-2, IL-4, IL-7, IL-9, IL-15 and IL-21 all signal via a common gamma chain in their cognate receptors and activate STAT5. Thus, in particular embodiments, a cytokine selected from IL-2, IL-4, IL-7, IL-9, IL-15 and IL-21, or a combination thereof, can be used in the methods of the present disclosure. In particular embodiments, IL-15 can be replaced with IL-2, IL-4, IL-7, IL-9 and/or IL-21. In particular embodiments, IL-15 can be supplemented with IL-2, IL-4, IL-7, IL-9 and/or IL-21.

IL-12, IL-23 and IL-35 share an IL-12Rb1 or IL-12Rb2 chain in their receptors and activate STAT4. Thus, in particular embodiments, a cytokine selected from IL-23 and IL-35, or a combination thereof, can be used in the methods of the present disclosure. In particular embodiments, IL-12 can be replaced with IL-23 and/or IL-35. In particular embodiments, IL-12 can be supplemented with IL-23 and/or IL-35.

IL-1, IL-18, IL-33 and IL-36, similar to Toll-like receptors, use Toll/interleukin-1 receptor (TIR) domains found in adapter protein MyD88 (myeloid differentiation primary response 88) for signaling. Thus, in particular embodiments, a cytokine selected from IL-1, IL-33 and IL-36, or a combination thereof, can be used in the methods of the present disclosure. In particular embodiments, IL-18 can be replaced with IL-1, IL-33, and/or IL-36. In particular embodiments, IL-18 can be supplemented with IL-1, IL-33, and/or IL-36.

In particular embodiments, one or more cytokines that can be used to create general inflammatory conditions in the absence of a TCR signal include effective amounts of IL-12, IL-2, and IL-1.

In particular embodiments, one or more cytokines that can be used to create general inflammatory conditions in the absence of a TCR signal include effective amounts of IL-12, IL-2, and IL-18.

In particular embodiments, one or more cytokines that can be used to create general inflammatory conditions in the absence of a TCR signal include effective amounts of IL-12, IL-2, and IL-33.

In particular embodiments, one or more cytokines that can be used to create general inflammatory conditions in the absence of a TCR signal include effective amounts of IL-12, IL-2, and IL-36.

In particular embodiments, one or more cytokines that can be used to create general inflammatory conditions in the absence of a TCR signal include effective amounts of IL-12, IL-4, and IL-1.

In particular embodiments, one or more cytokines that can be used to create general inflammatory conditions in the absence of a TCR signal include effective amounts of IL-12, IL-4, and IL-18.

In particular embodiments, one or more cytokines that can be used to create general inflammatory conditions in the absence of a TCR signal include effective amounts of IL-12, IL-4, and IL-33.

In particular embodiments, one or more cytokines that can be used to create general inflammatory conditions in the absence of a TCR signal include effective amounts of IL-12, IL-4, and IL-36.

In particular embodiments, one or more cytokines that can be used to create general inflammatory conditions in the absence of a TCR signal include effective amounts of IL-12, IL-7, and IL-1.

In particular embodiments, one or more cytokines that can be used to create general inflammatory conditions in the absence of a TCR signal include effective amounts of IL-12, IL-7, and IL-18.

In particular embodiments, one or more cytokines that can be used to create general inflammatory conditions in the absence of a TCR signal include effective amounts of IL-12, IL-7, and IL-33.

In particular embodiments, one or more cytokines that can be used to create general inflammatory conditions in the absence of a TCR signal include effective amounts of IL-12, IL-7, and IL-36.

In particular embodiments, one or more cytokines that can be used to create general inflammatory conditions in the absence of a TCR signal include effective amounts of IL-12, IL-9, and IL-1.

In particular embodiments, one or more cytokines that can be used to create general inflammatory conditions in the absence of a TCR signal include effective amounts of IL-12, IL-9, and IL-18.

In particular embodiments, one or more cytokines that can be used to create general inflammatory conditions in the absence of a TCR signal include effective amounts of IL-12, IL-9, and IL-33.

In particular embodiments, one or more cytokines that can be used to create general inflammatory conditions in the absence of a TCR signal include effective amounts of IL-12, IL-9, and IL-36.

In particular embodiments, one or more cytokines that can be used to create general inflammatory conditions in the absence of a TCR signal include effective amounts of IL-12, IL-15, and IL-1.

In particular embodiments, one or more cytokines that can be used to create general inflammatory conditions in the absence of a TCR signal include effective amounts of IL-12, IL-15, and IL-18.

In particular embodiments, one or more cytokines that can be used to create general inflammatory conditions in the absence of a TCR signal include effective amounts of IL-12, IL-15, and IL-33.

In particular embodiments, one or more cytokines that can be used to create general inflammatory conditions in the absence of a TCR signal include effective amounts of IL-12, IL-15, and IL-36.

In particular embodiments, one or more cytokines that can be used to create general inflammatory conditions in the absence of a TCR signal include effective amounts of IL-12, IL-21, and IL-1.

In particular embodiments, one or more cytokines that can be used to create general inflammatory conditions in the absence of a TCR signal include effective amounts of IL-12, IL-21, and IL-18.

In particular embodiments, one or more cytokines that can be used to create general inflammatory conditions in the absence of a TCR signal include effective amounts of IL-12, IL-21, and IL-33.

In particular embodiments, one or more cytokines that can be used to create general inflammatory conditions in the absence of a TCR signal include effective amounts of IL-12, IL-21, and IL-36.

In particular embodiments, one or more cytokines that can be used to create general inflammatory conditions in the absence of a TCR signal include effective amounts of IL-23, IL-2, and IL-1.

In particular embodiments, one or more cytokines that can be used to create general inflammatory conditions in the absence of a TCR signal include effective amounts of IL-23, IL-2, and IL-18.

In particular embodiments, one or more cytokines that can be used to create general inflammatory conditions in the absence of a TCR signal include effective amounts of IL-23, IL-2, and IL-33.

In particular embodiments, one or more cytokines that can be used to create general inflammatory conditions in the absence of a TCR signal include effective amounts of IL-23, IL-2, and IL-36.

In particular embodiments, one or more cytokines that can be used to create general inflammatory conditions in the absence of a TCR signal include effective amounts of IL-23, IL-4, and IL-1.

In particular embodiments, one or more cytokines that can be used to create general inflammatory conditions in the absence of a TCR signal include effective amounts of IL-23, IL-4, and IL-18.

In particular embodiments, one or more cytokines that can be used to create general inflammatory conditions in the absence of a TCR signal include effective amounts of IL-23, IL-4, and IL-33.

In particular embodiments, one or more cytokines that can be used to create general inflammatory conditions in the absence of a TCR signal include effective amounts of IL-23, IL-4, and IL-36.

In particular embodiments, one or more cytokines that can be used to create general inflammatory conditions in the absence of a TCR signal include effective amounts of IL-23, IL-7, and IL-1.

In particular embodiments, one or more cytokines that can be used to create general inflammatory conditions in the absence of a TCR signal include effective amounts of IL-23, IL-7, and IL-18.

In particular embodiments, one or more cytokines that can be used to create general inflammatory conditions in the absence of a TCR signal include effective amounts of IL-23, IL-7, and IL-33.

In particular embodiments, one or more cytokines that can be used to create general inflammatory conditions in the absence of a TCR signal include effective amounts of IL-23, IL-7, and IL-36.

In particular embodiments, one or more cytokines that can be used to create general inflammatory conditions in the absence of a TCR signal include effective amounts of IL-23, IL-9, and IL-1.

In particular embodiments, one or more cytokines that can be used to create general inflammatory conditions in the absence of a TCR signal include effective amounts of IL-23, IL-9, and IL-18.

In particular embodiments, one or more cytokines that can be used to create general inflammatory conditions in the absence of a TCR signal include effective amounts of IL-23, IL-9, and IL-33.

In particular embodiments, one or more cytokines that can be used to create general inflammatory conditions in the absence of a TCR signal include effective amounts of IL-23, IL-9, and IL-36.

In particular embodiments, one or more cytokines that can be used to create general inflammatory conditions in the absence of a TCR signal include effective amounts of IL-23, IL-15, and IL-1.

In particular embodiments, one or more cytokines that can be used to create general inflammatory conditions in the absence of a TCR signal include effective amounts of IL-23, IL-15, and IL-18.

In particular embodiments, one or more cytokines that can be used to create general inflammatory conditions in the absence of a TCR signal include effective amounts of IL-23, IL-15, and IL-33.

In particular embodiments, one or more cytokines that can be used to create general inflammatory conditions in the absence of a TCR signal include effective amounts of IL-23, IL-15, and IL-36.

In particular embodiments, one or more cytokines that can be used to create general inflammatory conditions in the absence of a TCR signal include effective amounts of IL-23, IL-21, and IL-1.

In particular embodiments, one or more cytokines that can be used to create general inflammatory conditions in the absence of a TCR signal include effective amounts of IL-23, IL-21, and IL-18.

In particular embodiments, one or more cytokines that can be used to create general inflammatory conditions in the absence of a TCR signal include effective amounts of IL-23, IL-21, and IL-33.

In particular embodiments, one or more cytokines that can be used to create general inflammatory conditions in the absence of a TCR signal include effective amounts of IL-23, IL-21, and IL-36.

In particular embodiments, one or more cytokines that can be used to create general inflammatory conditions in the absence of a TCR signal include effective amounts of IL-35, IL-2, and IL-1.

In particular embodiments, one or more cytokines that can be used to create general inflammatory conditions in the absence of a TCR signal include effective amounts of IL-35, IL-2, and IL-18.

In particular embodiments, one or more cytokines that can be used to create general inflammatory conditions in the absence of a TCR signal include effective amounts of IL-35, IL-2, and IL-33.

In particular embodiments, one or more cytokines that can be used to create general inflammatory conditions in the absence of a TCR signal include effective amounts of IL-35, IL-2, and IL-36.

In particular embodiments, one or more cytokines that can be used to create general inflammatory conditions in the absence of a TCR signal include effective amounts of IL-35, IL-4, and IL-1.

In particular embodiments, one or more cytokines that can be used to create general inflammatory conditions in the absence of a TCR signal include effective amounts of IL-35, IL-4, and IL-18.

In particular embodiments, one or more cytokines that can be used to create general inflammatory conditions in the absence of a TCR signal include effective amounts of IL-35, IL-4, and IL-33.

In particular embodiments, one or more cytokines that can be used to create general inflammatory conditions in the absence of a TCR signal include effective amounts of IL-35, IL-4, and IL-36.

In particular embodiments, one or more cytokines that can be used to create general inflammatory conditions in the absence of a TCR signal include effective amounts of IL-35, IL-7, and IL-1.

In particular embodiments, one or more cytokines that can be used to create general inflammatory conditions in the absence of a TCR signal include effective amounts of IL-35, IL-7, and IL-18.

In particular embodiments, one or more cytokines that can be used to create general inflammatory conditions in the absence of a TCR signal include effective amounts of IL-35, IL-7, and IL-33.

In particular embodiments, one or more cytokines that can be used to create general inflammatory conditions in the absence of a TCR signal include effective amounts of IL-35, IL-7, and IL-36.

In particular embodiments, one or more cytokines that can be used to create general inflammatory conditions in the absence of a TCR signal include effective amounts of IL-35, IL-9, and IL-1.

In particular embodiments, one or more cytokines that can be used to create general inflammatory conditions in the absence of a TCR signal include effective amounts of IL-35, IL-9, and IL-18.

In particular embodiments, one or more cytokines that can be used to create general inflammatory conditions in the absence of a TCR signal include effective amounts of IL-35, IL-9, and IL-33.

In particular embodiments, one or more cytokines that can be used to create general inflammatory conditions in the absence of a TCR signal include effective amounts of IL-35, IL-9, and IL-36.

In particular embodiments, one or more cytokines that can be used to create general inflammatory conditions in the absence of a TCR signal include effective amounts of IL-35, IL-15, and IL-1.

In particular embodiments, one or more cytokines that can be used to create general inflammatory conditions in the absence of a TCR signal include effective amounts of IL-35, IL-15, and IL-18.

In particular embodiments, one or more cytokines that can be used to create general inflammatory conditions in the absence of a TCR signal include effective amounts of IL-35, IL-15, and IL-33.

In particular embodiments, one or more cytokines that can be used to create general inflammatory conditions in the absence of a TCR signal include effective amounts of IL-35, IL-15, and IL-36.

In particular embodiments, one or more cytokines that can be used to create general inflammatory conditions in the absence of a TCR signal include effective amounts of IL-35, IL-21, and IL-1.

In particular embodiments, one or more cytokines that can be used to create general inflammatory conditions in the absence of a TCR signal include effective amounts of IL-35, IL-21, and IL-18.

In particular embodiments, one or more cytokines that can be used to create general inflammatory conditions in the absence of a TCR signal include effective amounts of IL-35, IL-21, and IL-33.

In particular embodiments, one or more cytokines that can be used to create general inflammatory conditions in the absence of a TCR signal include effective amounts of IL-35, IL-21, and IL-36.

Particular embodiments can include variants of interleukins disclosed or described herein. Variants include protein sequences having one or more additions, deletions, stop positions, or substitutions, as compared to the relevant reference sequence. An insertion, deletion or substitution may be anywhere in the interleukin protein, including at the amino- or carboxy-terminus or both ends of this region, provided that the modified interleukin protein can still induce MAIT cells to express CTLA-4 in the absence of a TCR signal. In particular embodiments, variants of IL-12, IL-15, and IL-18 protein sequences disclosed herein are also included. In particular embodiments, an IL-12, IL-15, or IL-18 protein of the present disclosure can include one or more insertions, one or more deletions, one or more amino acid substitutions (e.g., conservative amino acid substitutions or non-conservative amino acid substitutions), or a combination of the above-noted changes, when compared with the disclosed proteins (SEQ ID NOs: 1-10). A "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W. H. Freeman and Company.

Variants of interleukin protein sequences disclosed or described herein also include interleukin protein sequences with at least 70% sequence identity, 80% sequence identity, 85% sequence, 90% sequence identity, 95% sequence identity, 96% sequence identity, 97% sequence identity, 98% sequence identity, or 99% sequence identity to an interleukin protein described or disclosed herein.

"% sequence identity" refers to a relationship between two or more sequences, as determined by comparing the sequences. In the art, "identity" also means the degree of sequence relatedness between sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, NY. Within the context of this disclosure it will be understood that where sequence analysis software is used for analysis, the results of the analysis are based on the "default values" of the program referenced. "Default values" will mean any set of values or parameters, which originally load with the software when first initialized.

In particular embodiments, an effective amount of cytokines that create general inflammatory conditions includes 0.10 ng/mL to 200 ng/mL. In particular embodiments, an effective amount of each of the cytokines IL-12, IL-15 and IL-18 that create general inflammatory conditions includes 0.10 ng/mL to 200 ng/mL. In particular embodiments, an effective amount of each of cytokines IL-12, IL-15 and IL-18 includes 0.50 ng/mL to 150 ng/mL. In particular embodiments, an effective amount of each of cytokines IL-12, IL-15 and IL-18 includes 0.50 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 15 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 95 ng/mL, 100 ng/mL, 110 ng/mL, 120 ng/mL, 130 ng/mL, 140 ng/mL, 150 ng/mL, 160 ng/mL, 170 ng/mL, 180 ng/mL, 190 ng/mL, 200 ng/mL, or more. In particular embodiments, an effective amount of each of cytokines IL-12, IL-15 and IL-18 is 100 ng/mL. As indicated, these amounts of IL-12, IL-15 and IL-18 may be replaced by equivalent amounts of an interleukin substitute or supplement as described above.

In particular embodiments, an "effective duration of time" for incubation of MAIT cells in general inflammatory conditions in the absence of a TCR signal leads to MAIT cells that have an increase in CTLA-4 expression. In particular embodiments, an "effective duration of time" for incubation of MAIT cells in general inflammatory conditions in the absence of a TCR signal leads to MAIT cells with increased expression of CTLA-4 on the surface of the MAIT cells. In particular embodiments, an effective duration of time for stimulation of MAIT cells with IL-12, IL-15 and IL-18 in the absence of a TCR signal includes 5 minutes to 48 hours. In particular embodiments, an effective duration of time for stimulation of MAIT cells with IL-12, IL-15 and IL-18 in the absence of a TCR signal includes 10 minutes to 24 hours. In particular embodiments, an effective duration of time for stimulation of MAIT cells with IL-12, IL-15 and IL-18 in the absence of a TCR signal includes 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more. In particular embodiments, an effective duration of time for stimulation of MAIT cells with IL-12, IL-15 and IL-18 in the absence of a TCR signal is 5-10 hours. In particular embodiments, an effective duration of time for stimulation of MAIT cells with IL-12, IL-15 and IL-18 in the absence of a TCR signal is 6 hours. In particular embodiments, an effective duration of time for stimulation of MAIT cells with IL-12, IL-15 and IL-18 in the absence of a TCR signal is 24 hours. In particular embodiments, MAIT cells are induced to express CTLA-4 in the absence of a TCR signal after 6 hours of stimulation with IL-12, IL-15 and IL-18 followed by rest in culture. In particular embodiments, rest in culture is at least 12 hours. In particular embodiments, rest in culture is at least 18 hours. As indicated, these times for incubation can also apply to an interleukin substitute or supplement as described above.

(iii) Conditions for Absence of a TCR Signal in MAIT Cells. In particular embodiments, the absence of a TCR signal in MAIT cells occurs in a sterile culture medium. In particular embodiments, the absence of a TCR signal in MAIT cells occurs under sterile culture conditions. In particular embodiments, the absence of a TCR signal in MAIT cells occurs when MAIT cells are incubated in a culture with no added bacteria metabolites and no added yeast metabolites. In particular embodiments, the absence of a TCR signal in MAIT cells can be a complete absence of a TCR signal due to a sterile culture medium. In particular embodiments, the absence of a TCR signal in MAIT cells can be a complete absence of a TCR signal due to sterile culture conditions. In particular embodiments, the absence of a TCR signal in MAIT cells can be a complete absence of a TCR signal due to incubation in a culture with no added bacteria metabolites and no added yeast metabolites. In particular embodiments, the absence of a TCR signal in MAIT cells in a sterile culture medium can be a reduction in a TCR signal as compared to MAIT cells not in a sterile culture medium. In particular embodiments, the absence of a TCR signal in MAIT cells under sterile culture conditions can be a reduction in a TCR signal as compared to MAIT cells not under sterile culture conditions. In particular embodiments, the absence of a TCR signal in MAIT cells in a culture with no added bacteria metabolites and no added yeast metabolites can be a reduction in a TCR signal as compared to MAIT cells not in a culture with no added bacteria metabolites and no added yeast metabolites.

In particular embodiments, the absence of a TCR signal is due to inhibiting TCR signaling by incubating MAIT cells with an effective amount of an anti-MR1 antibody (Huang S et al. (2005) Journal of Biological Chemistry 280(22): 21183-21193). Anti-MR1 antibodies that are commercially available include: clone 26.5 (Biolegend, San Diego, CA); aa312-341, LS-C223326 (LifeSpan BioSciences, Seattle, WA); ARP78052_P050 (Aviva Systems Biology, San Diego, CA); and NBP2-57625 (Novus Biologicals, Littleton, CO). In particular embodiments, the absence of a TCR signal in MAIT cells can be a complete absence of a TCR signal due to incubation of MAIT cells with an effective amount of an anti-MR1 antibody. In particular embodiments, the absence of a TCR signal in MAIT cells incubated with an effective amount of an anti-MR1 antibody can be a reduction in a TCR signal as compared to MAIT cells not incubated with an effective amount of an anti-MR1 antibody.

In particular embodiments, an effective amount of an anti-MR1 antibody includes 0.10 µg/mL to 200 µg/mL. In particular embodiments, an effective amount of an anti-MR1 antibody includes 0.50 µg/mL to 100 µg/mL. In particular embodiments, an effective amount of an anti-MR1 antibody includes 0.50 µg/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 15 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, 80 µg/mL, 85 µg/mL, 90 µg/mL, 95 µg/mL, 100 µg/mL, 110 µg/mL, 120 µg/mL, 130 µg/mL, 140 µg/mL, 150 µg/mL, 160 µg/mL, 170 µg/mL, 180 µg/mL, 190 µg/mL, 200 µg/mL, or more. In particular embodiments, an effective amount of an anti-MR1 antibody is 50 µg/mL.

In particular embodiments, an effective duration of time of incubation of an anti-MR1 antibody with MAIT cells to confirm the effective reduction or absence of a TCR signal includes 5 minutes to 48 hours. In particular embodiments, an effective duration of time of incubation of an anti-MR1 antibody with MAIT cells to confirm the effective reduction or absence of a TCR signal includes 10 minutes to 24 hours. In particular embodiments, an effective duration of time of incubation of an anti-MR1 antibody with MAIT cells to confirm the effective reduction or absence of a TCR signal includes 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or more. In particular embodiments, an effective duration of time of incubation of an anti-MR1 antibody with MAIT cells to confirm the effective reduction or absence of a TCR signal is 5-10 hours. In particular embodiments, an effective duration of time of incubation of an anti-MR1 antibody with MAIT cells to confirm the effective reduction or absence of a TCR signal is 6 hours. In particular embodiments, an effective duration of time of incubation of an anti-MR1 antibody with MAIT cells to confirm the effective reduction or absence of a TCR signal is 24 hours.

(iv) Methods to Select for MAIT Cells. The sorting capabilities of a flow activated cell sorter (FACS) instrument can be used to isolate different cell populations. In particular embodiments, fluorescently labeled antibodies that bind cell surface molecules on immune cells can be used to positively or negatively select for immune cells with particular cell surface phenotypes. In particular embodiments, an anti-CD3 Pacific Blue antibody (clone OKT3, BioLegend, San Diego, CA), an anti-CD8 PerCPCy5.5 antibody (clone SK1, BD Biosciences, San Jose, CA), an anti-CD4 ECD antibody (clone SFCI12T4D11, Beckman Coulter, Brea, CA), an anti-CD161 PECy5 antibody (clone DX12, BD Biosciences, San Jose, CA), an anti-CCR6 APC antibody (clone R6H1, eBioscience, Waltham, MA), an anti-CD62L PE antibody (clone DREG-56, BD Biosciences, San Jose, CA), and/or an anti-Vα7.2 PE antibody (clone 3C10, BioLegend, San Diego, CA) can be used in flow cytometric assays to select for MAIT cells, CD4$^+$ cells, CD8$^+$ cells, and Treg cells. In particular embodiments, selected live MAIT cells have a CD3$^+$CD4$^-$CD8$^+$Vα7.2$^+$CD161$^{hi}$ phenotype. In particular embodiments, selected live MAIT cells have a CD8$^+$CD161$^{hi}$CCR6$^{hi}$CD62L$^{lo}$ phenotype. In particular embodiments, selected live CD4$^+$ cells have a CD3$^+$CD4$^+$CD8$^-$Foxp3$^-$Helios$^-$ phenotype. In particular embodiments, selected live CD8$^+$ cells have a CD3$^+$CD4$^-$CD8$^+$Vα7.2$^-$CD161$^-$ phenotype. In particular embodiments, selected live Treg cells have a CD3$^+$CD4$^+$CD8$^-$CD25$^{hi}$IL-7rα$^{lo}$Foxp3$^+$Helios$^+$ phenotype. The sorted cells can be recovered in a viable state for further biochemical processing or culture.

(v) Assays to Measure CTLA-4 expression and MAIT Cell Modulation. Methods to measure expression of CTLA-4 inhibitory cell surface receptor described herein are well known to one of ordinary skill in the art. Such methods include ELISA (enzyme linked immunosorbent assay), western blot, flow activated cell sorting (FACS), radioimmunological assay (RIA); sandwich assay; fluorescent in situ hybridization (FISH); immunohistological staining; immunoelectrophoresis; immunoprecipitation, and immunofluorescence using detection reagents such as an antibody or protein binding agents.

In particular embodiments, an assay to measure CTLA-4 expression is RNA-seq (RNA sequencing), a methodology that allows quantification, discovery and profiling of RNAs based on next-generation sequencing (NGS). For this technique, mRNA (and other RNAs) are first converted to cDNA in preparation for generation of a library for sequencing. RNA-seq provides digital data in the form of aligned read-counts.

In particular embodiments, the assay to measure CTLA-4 expression is flow cytometry (FACS). Flow cytometry is a technology that characterizes populations of cells, on a cell-by-cell basis, in terms of their fluorescence properties. Several different fluorescent signals can be monitored simultaneously and independently. Fluorescence is the fundamental parameter evaluated by a flow cytometer, so gene expression can be quantified by flow cytometry. The intensity of fluorescence serves as an indication for the number of protein molecules synthesized from a particular gene expressed by a cell or introduced into the cell. The intensity of the fluorescence is, in general, linearly related to the expression from a gene of interest, so the FACS can quantify directly, on a cell-by-cell basis, the translation/transcription activity of a gene of interest. The measurement is made on each cell independently, so the analysis of a cell population can be displayed as a distribution of activities. Thus, heterogeneous gene expression within a population can be resolved; for example, the presence of a few cells highly expressing one or more genes of interest is easily detected amongst a majority of nonexpressing cells.

In particular embodiments, an anti-CD25 BV421 antibody (clone M-A251, BD Biosciences, San Jose, CA), an anti-CD3 BUV661 antibody (clone UCHT1, BD Biosciences, San Jose, CA), an anti-CD8 BUV805 antibody (clone SK1, BD Biosciences, San Jose, CA), an anti-CD4 APCR700 antibody (clone RPA-T4, BD Biosciences, San Jose, CA), an anti-CD161 BV605 antibody (clone DX12, BD Biosciences, San Jose, CA), an anti-Vα7.2 PE antibody (clone 3C10, BioLegend, San Diego, CA), an anti-IL-7Rα BV786 antibody (clone HIL-7R-M21, BD Biosciences, San Jose, CA), an anti-Foxp3 Alexa Fluor 488 antibody (clone 259D/C7, BD Biosciences, San Jose, CA), an anti-Helios PerCP-eFluor 710 antibody (clone 22F6, Invitrogen, Carlsbad, CA), and/or an anti-CTLA-4 PECF594 antibody (BNI3, BD Biosciences, San Jose, CA) are used in flow cytometric assays to phenotype immune cells and measure CTLA-4 expression on the phenotyped immune cells. In particular embodiments, the immune cells include MAIT cells, $CD4^+$ cells, $CD8^+$ cells, and Treg cells.

In particular embodiments, a representative protocol for MAIT cell modulation is described in Slichter, C K et al. (2016) JCI insight, 1(8) and Dias J et al. (2016) Journal of leukocyte biology 100(1): 233-240, and can include assessing MAIT cell activation by measuring CD69 and/or CD25 expression by flow cytometry using an anti-CD69 antibody (e.g, a fluorochrome conjugated anti-CD69, clone FN50, BioLegend, San Diego, CA) and/or an anti-CD25 antibody (e.g., anti-CD25 BV421, clone M-A251, BD Biosciences, San Jose, CA).

In particular embodiments, MAIT cell modulation can be assessed by measuring expression of cytokines, cytolytic molecules, and/or chemokines. MAIT cells stimulated by general inflammatory conditions can be analyzed by FACS and Luminex (Luminex Corp., Austin, TX) to measure expression of cytokines, cytolytic molecules, and/or chemokines. IFNγ and CCL3 concentrations within supernatants can be assessed by Luminex according to the manufacturer's instructions. Secretion of IFNγ and Granzyme B can be measured by flow cytometry using an anti-IFNγ antibody (e.g., anti-IFNγ, eFluor® 450, clone 4S.b3, eBioscience, Waltham, MA) and an anti-Granzyme B antibody (e.g., anti-Granzyme B PE, clone GB11, eBioscience, Waltham, MA), respectively.

(vi) Kits. Combinations of elements that can be used to induce expression of CTLA-4 on the surface of MAIT cells in the absence of a TCR signal can also be provided as kits. Kits can include one or more of: MAIT cells; an effective amount of one or more cytokines; and one or more reagents to detect expression of CTLA-4. In particular embodiments, the MAIT cells are in a population of mononuclear cells. In particular embodiments, the mononuclear cells are PBMCs. In particular embodiments, the one or more cytokines include IL-12, IL-15, and IL-18. In particular embodiments, a kit can further include an effective amount of an anti-MR1 antibody. In particular embodiments, a kit can further include at least one antibody to select for or to phenotype MAIT cells. In particular embodiments, an anti-CD25 antibody, an anti-CD3 antibody, an anti-CD8 antibody, an anti-CD4 antibody, an anti-CD161 antibody, an anti-CCR6 antibody, an anti-CD62L antibody, an anti-Vα7.2 antibody, an anti-IL-7Rα antibody, an anti-Foxp3 antibody, and/or an anti-Helios antibody may be included as part of a kit to select for or to phenotype MAIT cells. In particular embodiments, the one or more reagents to detect expression of CTLA-4 includes an anti-CTLA4 antibody and/or one or more oligonucleotides binding CTLA-4 polynucleotide. In particular embodiments, the anti-CTLA4 antibody is fluorescently labeled. The kits may be used to produce MAIT cells induced to express CTLA-4 in the absence of a TCR signal.

The kits can further include instructions for using the kit, for example, instructions regarding preparation of MAIT cells; selection or phenotyping of MAIT cells with fluorescently labeled antibodies; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In particular embodiments, kits can also include some or all of the necessary laboratory supplies needed to use the kit effectively, such as cell culture media, buffers, enzymes, sterile plates, sterile flasks, pipettes, gloves, and the like. Variations in contents of any of the kits described herein can be made.

The Exemplary Embodiments and Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Exemplary Embodiments

1. A method of inducing expression of CTLA-4 on MAIT cells in the absence of a T cell receptor (TCR) signal including incubating MAIT cells in general inflammatory conditions for an effective duration of time, thereby inducing expression of CTLA-4 on MAIT cells in the absence of a TCR signal.
2. A method of modulating MAIT cell function in the absence of a T cell receptor (TCR) signal including exposing MAIT cells to general inflammatory conditions for an effective duration of time, thereby inducing expression of CTLA-4 on MAIT cells in the absence of a TCR signal.
3. A method of embodiment 2, wherein modulating MAIT cell function includes reducing activation of MAIT cells.
4. A method of embodiment 3, wherein reducing activation of MAIT cells includes reducing activation to 25% or less as compared to a positive activated MAIT cell control.
5. A method of any of embodiments 2-4, wherein modulating MAIT cell function includes reducing expression of CD69 and/or CD25 on MAIT cells by 75% or more.
6. A method of any of embodiments 2-5, wherein modulating MAIT cell function includes reducing the percentage of MAIT cells that secrete one or more cytokines, one or more cytolytic molecules, one or more chemokines, or a combination thereof.
7. A method of any of embodiments 2-6, wherein modulating MAIT cell function includes reducing secretion of one or more cytokines, one or more cytolytic molecules, one or more chemokines, or a combination thereof.
8. A method of embodiment 6 or 7, wherein the one or more cytokines includes IFNγ, the one or more cytolytic molecules includes granzyme B, and the one or more chemokines includes CCL3.
9. A method of any of embodiments 6-8, wherein the percentage of MAIT cells that secrete granzyme B is reduced to 70% or less as compared to a positive activated MAIT cell control.
10. A method of embodiment any of embodiments 6-9, wherein the percentage of MAIT cells that secrete IFNγ is reduced to 70% or less as compared to a positive activated MAIT cell control.
11. A method of any of embodiments 1-10, wherein the effective duration of time is 24 hours.
12. A method of inducing expression of CTLA-4 on MAIT cells in the absence of a T cell receptor (TCR) signal including:
incubating MAIT cells in general inflammatory conditions and under sterile conditions for a first effective duration of time;
removing the general inflammatory conditions;
washing the MAIT cells with culture media;
resuspending the MAIT cells in culture media; and
resting the MAIT cells in culture for a second effective duration of time, thereby inducing expression of CTLA-4 on MAIT cells in the absence of a TCR signal.
13. A method of modulating MAIT cell function in the absence of a T cell receptor (TCR) signal including:
exposing MAIT cells in general inflammatory conditions and under sterile conditions for a first effective duration of time;
removing the general inflammatory conditions;
washing the MAIT cells with culture media;
resuspending the MAIT cells in culture media; and
resting the MAIT cells in culture for a second effective duration of time, thereby modulating MAIT cell function in the absence of a TCR signal.
14. A method of embodiment 13, wherein modulating MAIT cell function includes reducing activation of MAIT cells.
15. A method of embodiment 14, wherein reducing activation of MAIT cells includes reducing activation to 25% or less as compared to a positive activated MAIT cell control.
16. A method of any of embodiments 13-15, wherein modulating MAIT cell function includes reducing expression of CD69 and/or CD25 on MAIT cells by 75% or more.
17. A method of any of embodiments 13-16, wherein modulating MAIT cell function includes reducing the percentage of MAIT cells that secrete one or more cytokines, one or more cytolytic molecules, one or more chemokines, or a combination thereof.
18. A method of any of embodiments 13-17, wherein modulating MAIT cell function includes reducing secretion of one or more cytokines, one or more cytolytic molecules, one or more chemokines, or a combination thereof.
19. A method of embodiment 17 or 18, wherein the one or more cytokines includes IFNγ, the one or more cytolytic molecules includes granzyme B, and the one or more chemokines includes CCL3.
20. A method of any of embodiments 17-19, wherein the percentage of MAIT cells that secrete granzyme B is reduced to 70% or less as compared to a positive activated MAIT cell control.
21. A method of any of embodiments 17-20, wherein the percentage of MAIT cells that secrete IFNγ is reduced to 70% or less as compared to a positive activated MAIT cell control.
22. A method of any of embodiments 12-21, wherein the first effective duration of time includes 5-10 hours.
23. A method of any of embodiments 12-22, wherein the second effective duration of time includes at least 12 hours.
24. A method of any of embodiments 12-23, wherein the culture media includes RPMI 1640 supplemented with 100 U/ml penicillin, 100 μg/ml streptomycin sulfate, and 10% FBS.
25. A method of any of embodiments 1-24, wherein the general inflammatory conditions include an effective amount of each of one or more cytokines including IL-1, IL-2, IL-4, IL-7, IL-9, IL-12, IL-15, IL-18, IL-21, IL-23, IL-33, IL-35, and IL-36.
26. A method of any of embodiments 1-25, wherein the general inflammatory conditions include an effective amount of each of one or more cytokines including IL-12, IL-15, and IL-18.
27. A method of any of embodiments 1-26, wherein the effective amount of each of one or more cytokines includes 100 ng/mL.
28. A method of any of embodiments 1-27, wherein the method further includes incubating the MAIT cells with an effective amount of an anti-MR1 antibody.
29. A method of embodiment 28, wherein the effective amount of the anti-MR1 antibody includes 50 μg/m L.
30. A method of any of embodiments 1-29, wherein the MAIT cells are in a population of mononuclear cells.
31. A method of any of embodiments 1-30, wherein the MAIT cells are selected or phenotyped using the presence or absence of cell surface markers selected from CD3, CD4, CD8, Vα7.2, CD161, CCR6, CD62L, or a combination thereof.
32. A method of any of embodiments 1-31, wherein the MAIT cells are $CD3^+CD4^-CD8^+V\alpha7.2^+CD161^{hi}$.
33. A method of any of embodiments 1-32, wherein the MAIT cells are $CD8^+CD161^{i}CCR6^{hi}CD62L^{lo}$.
34. A method of any of embodiments 1-33, wherein the method produces MAIT cells programmed to express CTLA-4.
35. A kit including one or more of:
an effective amount of one or more reagents to create general inflammatory conditions; and one or more reagents to detect expression of CTLA-4.
36. A kit of embodiment 35 further including MAIT cells.
37. A kit of embodiment 36, wherein the MAIT cells are in a population of mononuclear cells.
38. A kit of embodiment 37, wherein the mononuclear cells include peripheral blood mononuclear cells (PBMCs).
39. A kit of any of embodiments 35-38, wherein the effective amount of one or more reagents to create general inflammatory conditions include an effective amount of each of one or more cytokines including IL-1, IL-2, IL-4, IL-7, IL-9, IL-12, IL-15, IL-18, IL-21, IL-23, IL-33, IL-35, and IL-36.
40. A kit of any of embodiments 35-39, wherein the effective amount of one or more reagents to create general inflammatory conditions include an effective amount of each of one or more cytokines including IL-12, IL-15, and IL-18.
41. A kit of embodiment 39 or 40, wherein the effective amount of each of one or more cytokines includes 100 ng/mL.
42. A kit of any of embodiments 35-41, further including an effective amount of an anti-MR1 antibody.
43. A kit of embodiment 42, wherein the effective amount of the anti-MR1 antibody includes 50 µg/mL.
44. A kit of any of embodiments 35-43, further including at least one antibody to select for or to phenotype MAIT cells.
45. A kit of embodiment 44, wherein the at least one antibody includes an anti-CD25 antibody, an anti-CD3 antibody, an anti-CD8 antibody, an anti-CD4 antibody, an anti-CD161 antibody, an anti-CCR6 antibody, an anti-CD62L antibody, an anti-Vα7.2 antibody, an anti-IL-7Rα antibody, an anti-Foxp3 antibody, an anti-Helios antibody, or combination thereof.
46. A kit of embodiment 44 or 45, wherein the at least one antibody includes at least one fluorescently labeled antibody.
47. A kit of any of embodiments 35-46, wherein the one or more reagents to detect expression of CTLA-4 includes an anti-CTLA4 antibody and/or one or more oligonucleotides binding CTLA-4 polynucleotide.
48. A kit of embodiment 47, wherein the anti-CTLA4 antibody is fluorescently labeled.
49. A kit of any of embodiments 35-48, further including cell culture media, sterile plates, sterile flasks, buffers and/or enzymes.

Example 1. MAIT cells and CTLA-4 expression. T cells are an important component of the adaptive immune system that are usually characterized as CD4$^+$ (helper) or CD8+ (cytotoxic). MAIT cells are a recently characterized subset of unconventional T cells that recognize bacterial products via the TCR. MAIT cells are located in blood and tissues, including mucosal tissues with microbiomes such as the gut. It is unclear how MAIT cells are regulated at mucosal surfaces given the cells' continuous exposure to microbiomes. Human mucosa and matched blood were used to study MAIT cells and mechanisms of CTLA-4 function.

Materials and Methods. Cell isolation from mucosal tissues. Oral mucosa (gingival) specimens along with oral blood from the incision site were obtained from patients undergoing periodontic surgery. After extraction, tissue and blood samples were immediately placed in RPMI 1640 (supplemented with penicillin at 100 U/ml, streptomycin sulfate at 100 µg/ml, and fetal bovine serum (FBS) at 10% on ice for transport. Mononuclear cells from mucosal tissue were extracted after 2 rounds of mechanical digestion with a 30 cc syringe and blunt 16-gauge needle and enzymatic digestion with collagenase II (Sigma-Aldrich). Oral blood was treated with Ammonium-Chloride-Potassium (ACK) lysing buffer to remove red blood cells and isolate mononuclear cells. Cell were then stained for single cell sorting and RNA sequencing.

Flow cytometry. For phenotypic identification used in cell sorting and CTLA-4 induction assay, bulk peripheral mononuclear cells (PBMCs) or isolated mononuclear cells from tissue were stained with Aqua Live/Dead Fixable Dead Cell Stain (Invitrogen, Carlsbad, CA) and a combination of the following antibodies: (1) Cell Sorting—CD3 Pacific Blue (clone OKT3, BioLegend, San Diego, CA), CD8 PerCPCy5.5 (clone SK1, BD Biosciences, San Jose, CA), CD4 ECD (clone SFCI12T4D11, Beckman Coulter, Brea, CA), CD161 PECy5 (clone DX12, BD Biosciences, San Jose, CA), CCR6 APC antibody (clone R6H1, eBioscience, Waltham, MA), CD62L PE antibody (clone DREG-56, BD Biosciences, San Jose, CA), Vα7.2 PE (clone 3C10, BioLegend, San Diego, CA); (2) CTLA-4 induction assay—CD25 BV421 (clone M-A251, BD Biosciences, San Jose, CA), CD3 BUV661 (clone UCHT1, BD Biosciences, San Jose, CA), CD8 BUV805 (clone SK1, BD Biosciences, San Jose, CA), CD4 APCR700 (clone RPA-T4, BD Biosciences, San Jose, CA), CD161 BV605 (clone DX12, BD Biosciences, San Jose, CA), Vα7.2 PE (clone 3C10, BioLegend, San Diego, CA), IL-7Rα BV786 (clone HIL-7R-M21, BD Biosciences, San Jose, CA), Foxp3 Alexa Flour 488 (clone 259D/C7, BD Biosciences, San Jose, CA), Helios PerCP-eFluor 710 (clone 22F6, Invitrogen, Carlsbad, CA), CTLA-4 PECF594 (BNI3, BD Biosciences, San Jose, CA). Sorting experiments were performed on a FACS Aria II (BD Biosciences, San Jose, CA) and phenotyping for CTLA-4 induction assays were performed on FACSymphony (BD Biosciences, San Jose, CA). Data was analyzed using Flowjo software (version 10.4.1).

RNA sequencing. MAIT cells were sorted as live CD3$^+$CD4$^-$CD8$^+$Vα7.2$^+$CD161$^{hi}$ cells from mucosal tissue and oral blood and processed with SMARTseq v4 kit (Clontech, Mountain View, CA). RNA-seq library generation. RNA-seq was performed on 100-1000 sorted CD8$^+$ MAIT cells from blood or tissue samples. In total, 22 samples were sequenced, 10 from blood and 11 from tissue. Cells were sorted directly into SMARTer® v3 lysis reagents (Clontech, Mountain View, CA). Cells were lysed and cDNA was synthesized. After amplification, sequencing libraries were prepared using the Nextera XT DNA Library Preparation Kit (Illumina, San Diego, CA). Barcoded single-cell libraries were pooled and quantified using a Qubit® Fluorometer (Life Technologies, Carlsbad, CA).

Sequencing and alignment of libraries. Single-read sequencing of the libraries was carried out either on a HiSeq2500 sequencer (Illumina, San Diego, CA) with 58-base pair reads, using TruSeq v4 Cluster and SBS kits (Illumina, San Diego, CA) with a target depth of 2.5 million reads for single cells and 5 million reads for bulk libraries. Base-calling was performed automatically in Illumina BaseSpace after sequencing; FASTQ reads were trimmed in a local Galaxy server in two steps. First, hard-trimming was applied to remove one 3'-end base (FASTQ Trimmer tool, v.1.0.0). Second, quality trimming from both ends was applied until a minimum base quality for each read of at least 30 was obtained (FASTQ Quality Trimmer tool, v.1.0.0) (Landmead 2009, PMID:16169926). Reads were aligned to the University of California Santa Cruz (UCSC) Human genome assembly version 19 in Galaxy using Bowtie and TopHat (Tophat for Illumina tool, v.1.5.0) (PMID: 20161021). Read counts by Ensembl gene ID were obtained in Galaxy using htseq-count (htseq-count tool, v.0.4.1) (PMID: 25260700).

RNA-seq analysis. A quality filter was applied to retain libraries prepared with at least 225 cells, in which the fraction of unpaired reads examined compared to total FASTQ reads was >75%, the median coefficient of variation of coverage was less than 0.8, and the library had at least 500,000 reads. Sixteen of the 22 sequenced samples passed these quality filters. Non-protein coding genes, mitochondrial genes, and genes expressed at less than 1 count per million in fewer than 10% of samples were filtered out. Expression counts were normalized using the TMM algorithm (PMID: 20196867). For differential gene expression analysis, we used the linear models for microarray data (Limma) R package (PMID: 25925576, 25605792) after Voom transformation (PMID: 24485249). A linear model comparing blood and tissue sample gene expression including donor identity as a random effect was used. Genes with a false discovery rate of less than 0.05 and expression fold-change of greater than 2 between two blood and tissue samples were considered differentially expressed.

Monocyte *E. coli* stimulation and MAIT culture. CD14$^+$ monocytes were isolated using a CD14 positive isolation kit and either left untreated or fed formaldehyde-fixed *E. coli* (K-12, ATCC) at a ratio of 10 bacteria to one cell. Bacteria and monocytes were incubated for 30 minutes, after which fixed bacteria were washed off with R10 media (RPMI 1640+10% FBS+supplements), followed by an additional 2 hour incubation at 37° C. Monocytes were counted and plated at a 2:1 ratio to sorted MAIT cells and cultured for 24 hours at 37° C. in the presence or absence of 50 µg/mL of an anti-MR1 blocking antibody (clone 26.5, Biolegend, San Diego, CA). Following culture MAIT cells were analyzed for activation (CD25 and/or CD69 expression) by flow cytometry.

CTLA-4 induction assay. Cryopreserved PBMCs were thawed and left untreated in RPMI 1640 (supplemented as described above) or stimulated with cytokines, stimulated through the T-cell receptor (TCR), or stimulated by a combination of both treatments. Cytokine stimulation was performed using IL-12 (Invitrogen, Carlsbad, CA), IL-15 (Invitrogen, Carlsbad, CA), and IL-18 (MBLI, Woburn, MA) at 100 ng/mL. TCR stimulation was done using Dynabead Human T cell activator (Invitrogen, Carlsbad, CA) anti-CD3/CD28 beads at a 1:1 bead/T cell ratio. Whole PBMCs were left unstimulated or stimulated at a concentration of $1.25 \times 10^6$ per well using a 96-well plate for 6 and 24 hours at 37° C. to allow expression of CTLA-4. MAIT cells only stimulated for 6 hours needed a minimal 12 hours of rest in culture for sufficient induction of CTLA-4. Cytokines and TCR beads were removed by magnetic extraction and washing. Briefly, Dynabeads were removed using EasySep™ Magnet (STEMCELL Technologies Inc., Cambridge, MA). Cells were moved into 5 mL round bottom polystyrene tubes and 0.5 mL of 1×PBS (phosphate buffered saline) was added to each tube. Each tube was placed in an EasySep™ magnet for 1 min. Keeping the tube inside the magnet, the entire contents of the tube were poured into another tube outside of the magnet. The magnetic Dynabeads remained in the first tube inside the EasySep™ magnet, while cells were moved into the new tube. Cells were washed twice by centrifuging at 2000 rpm for 3 min and resuspending in 200 µL RPMI 1640 (supplemented as described above). After the washes, the cells were resuspended in 200 µL of RPMI 1640 (supplemented as described above) before transferring back into a 96-well plate to rest in culture. To block TCR signaling, cells in "cytokine only" condition were treated with an anti-MR1 antibody (clone 26.5, Biolegend, San Diego, CA) at 50 µg/mL. Cells were then stained with antibodies for flow cytometric acquisition and analysis as outlined above.

Phenotypic identification of T cells. MAIT cells were identified as live CD3$^+$CD4$^-$CD8$^+$Vα7.2$^+$CD161$^{hi}$ cells. Conventional CD8+ cells were identified as live CD3$^+$CD4$^-$CD8$^+$Vα7.2$^-$CD161$^-$ cells. Regulatory T cells (Treg) were identified as live CD3$^+$CD4$^+$CD8$^-$CD25$^{hi}$IL-7rα$^{lo}$Foxp3$^+$Helios$^+$ cells. Convectional CD4$^+$ cells were identified as live CD3$^+$CD4$^+$CD8$^-$Foxp3$^-$Helios$^-$ cells.

Detection of CTLA-4. After each T cell population was initially identified using flow cytometric analysis, CTLA-4 expression was determined using the "no stimulation" condition of the conventional CD8$^+$ subset as a negative control for gating strategy.

Figure 2A:
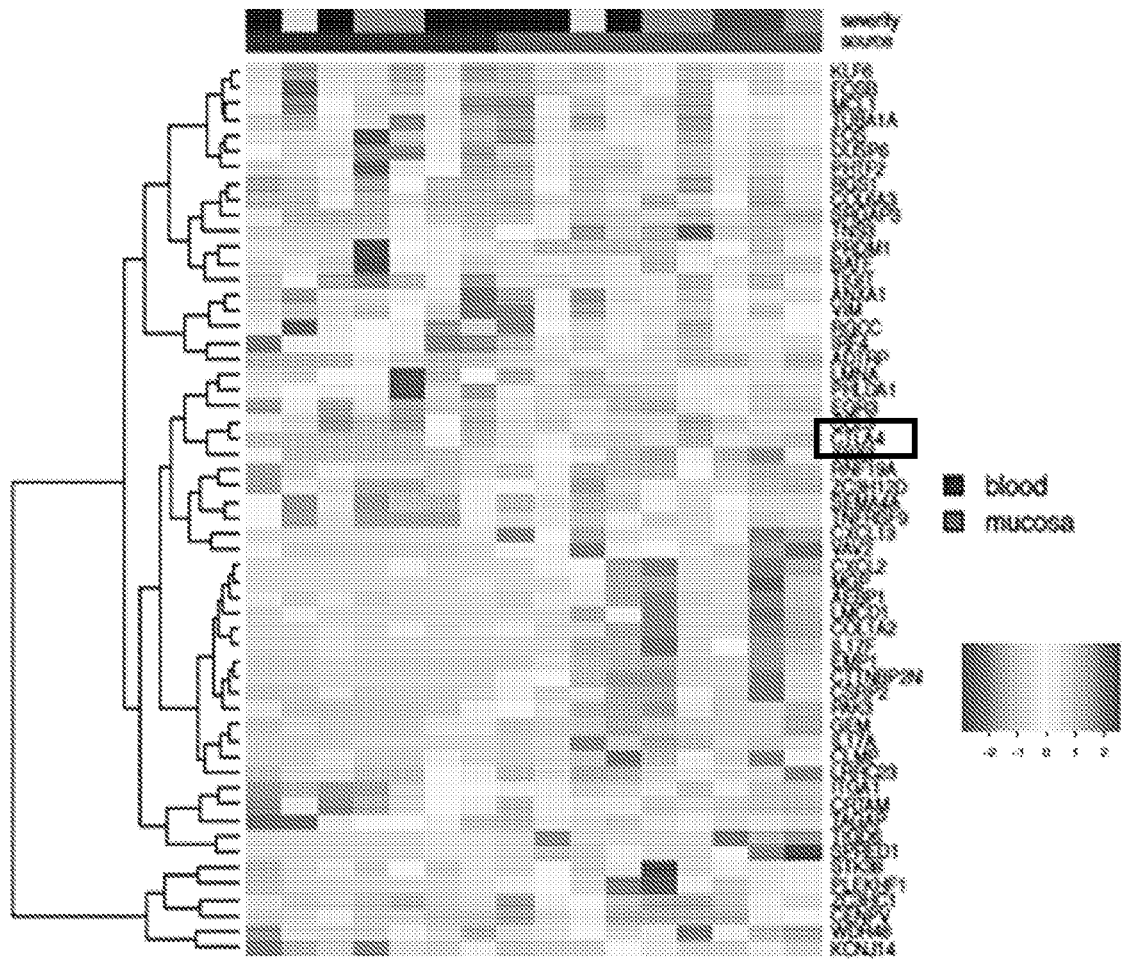
FIG. 2A shows a heat map with top genes differentially expressed between MAIT cells from mucosa and blood. MAIT cells from mucosa and blood were sorted (CD3$^+$CD4$^-$CD8$^+$Vα7.2$^+$CD161$^{hi}$) for RNA sequencing (n=7 for blood and n=10 for mucosa). CTLA-4 is highlighted with a box.
Figure 2B:
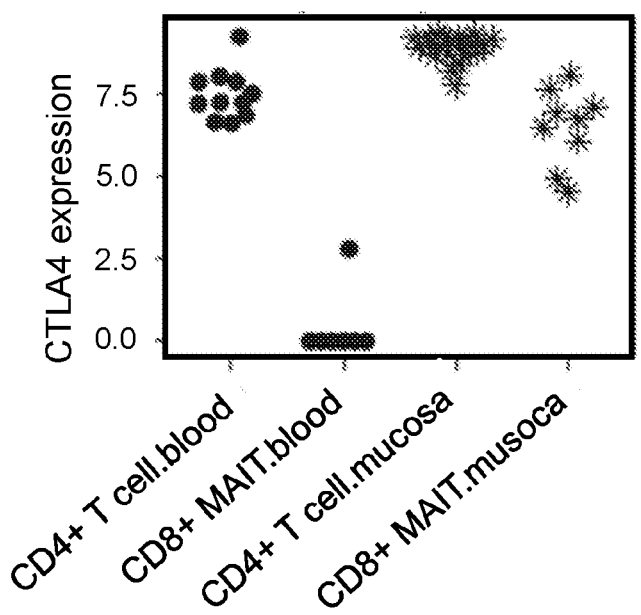
FIG. 2B shows RNA expression for CTLA-4 in MAIT cells and CD4$^+$ T cells (CD3$^+$CD4$^+$CD8$^-$Foxp3$^-$Helios$^-$) in blood and tissue from the same experiment described in FIG. 2A. CTLA-4 RNA expression is indicated as read counts relative to samples with no CTLA-4 expression.

Results. MAIT cells from mucosa and blood were sorted as live CD3$^+$CD4$^-$CD8$^+$Vα7.2$^+$CD161$^{hi}$ cells for RNA sequencing (n=7 for blood and n=10 for mucosa). Top genes differentially expressed between MAIT cells from mucosa and blood are shown in a heat map in FIG. 2A. One of the top genes expressed on MAIT cells in mucosa is CTLA-4, highlighted by a box in the heat map (FIG. 2A). Similar to CD4+ T cells in blood and mucosa, MAIT cells in mucosa had increased RNA expression of CTLA-4 as compared to CD8+ cells in blood (FIG. 2B).

Figure 3B:
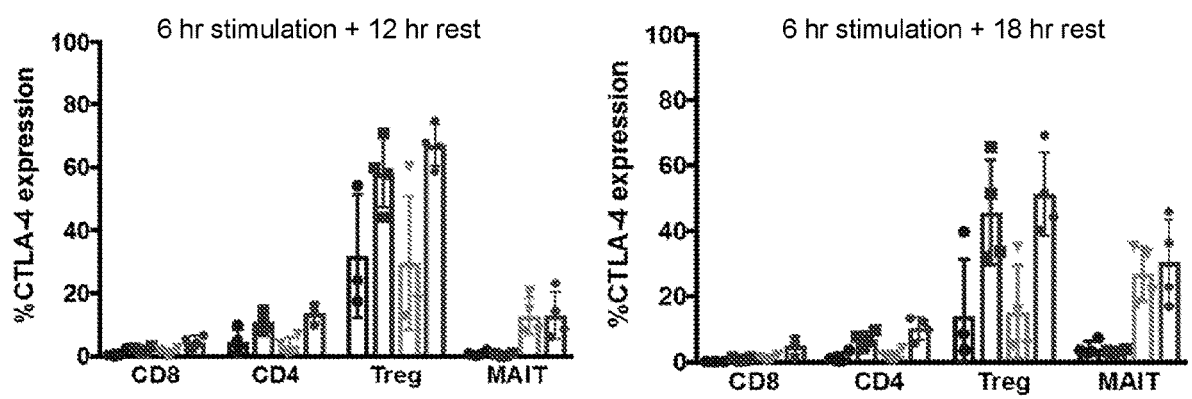
FIG. 3B shows the percentage of cells in each indicated T cell subset that are positive for CTLA-4 expression after a 6-hour stimulation with the indicated signal(s) and 12 hours rest (left-hand graph) and after a 6-hour stimulation with the indicated signal(s) and 18 hours rest (right-hand graph). NS=no stimulation; TCR=stimulation through TCR signal; IL12/15/18=stimulation with cytokines IL-12, IL-15, IL-18; TCR+IL12/15/18=stimulation through both TCR signal and cytokines IL-12, IL-15, IL-18.
Figure 4:
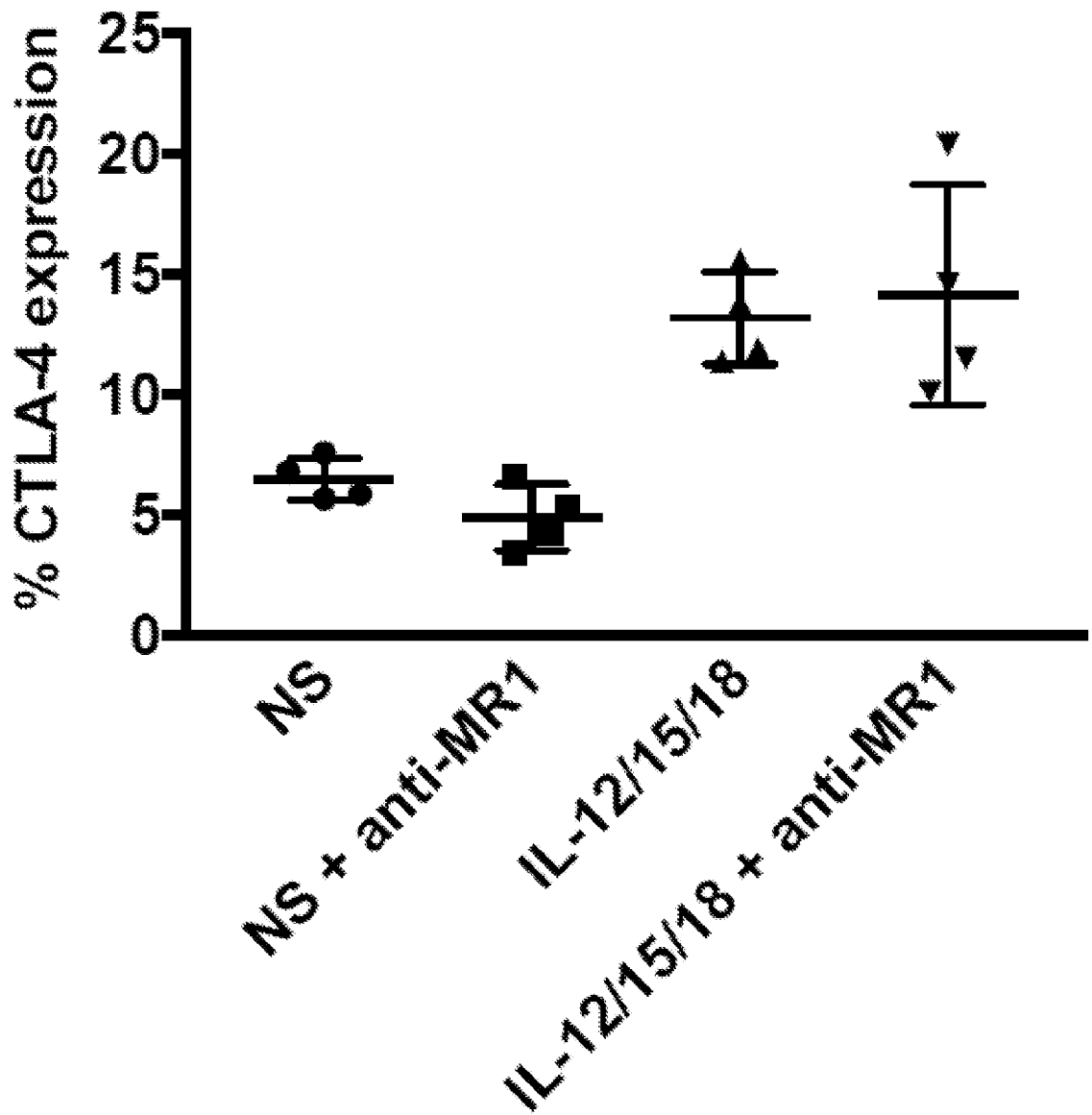
FIG. 4 shows CTLA-4 expression on MAIT cells in no stimulation (NS) and IL-12/15/18 conditions with and without anti-MR1 blocking antibodies.
Figure 5A:
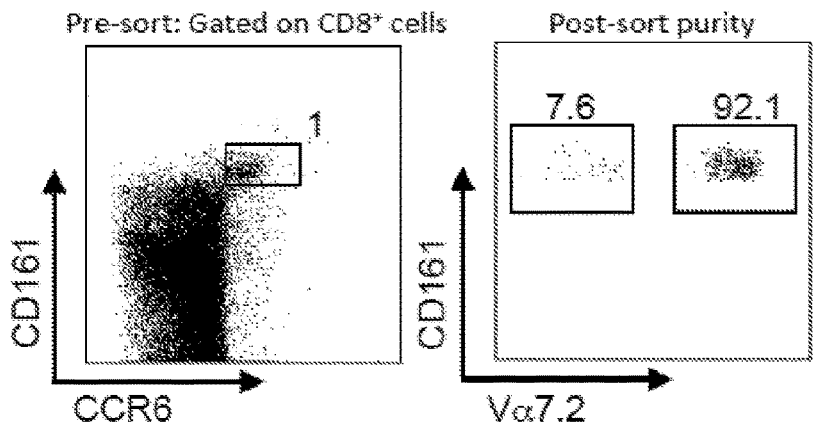
FIGS. 5A-5E demonstrates the blocking properties of an anti-MR1 antibody.
Figure 5B:
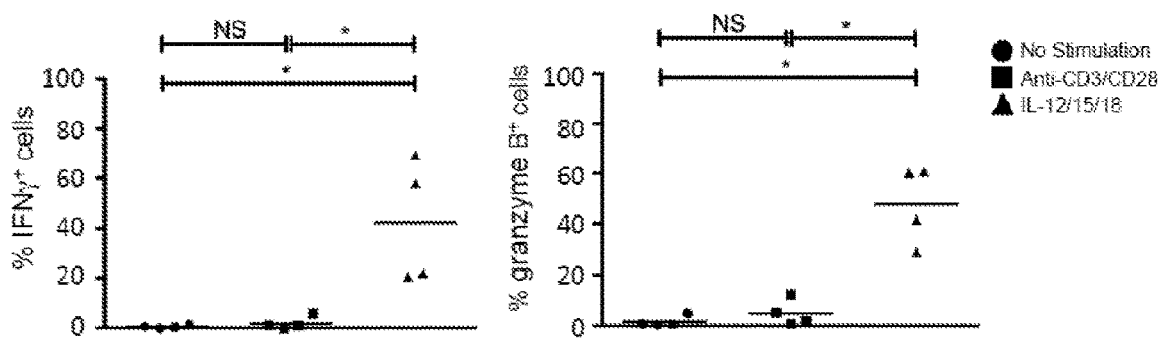
Figure 5C:
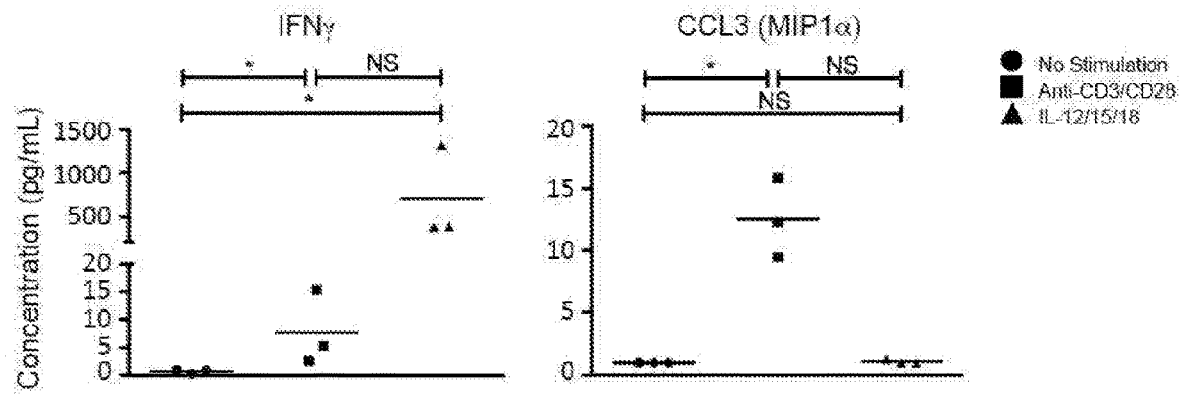
Figure 5D:
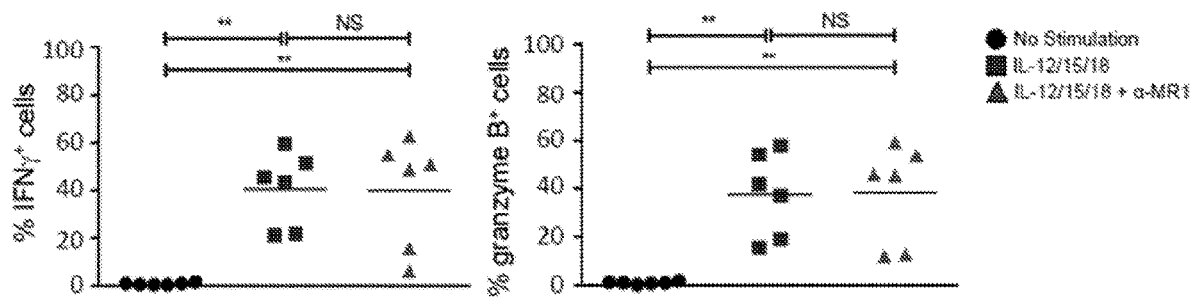
Figure 5E:
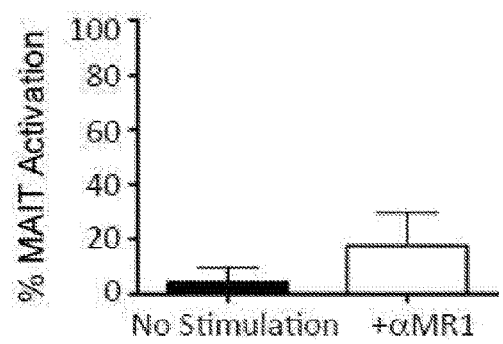

To assess what signals induce MAIT cells to express CTLA-4, PBMCs were stimulated for 24 hours in four conditions: no stimulation; stimulation through TCR; stimulation with cytokines IL-12, IL-15 and IL-18; and stimulation through both TCR and cytokines IL-12, IL-15 and IL-18. Cells were stained for CTLA-4 and markers characteristic of MAIT cells (CD3$^+$CD4$^-$CD8$^+$Vα7.2$^+$CD161$^{hi}$) or regulatory T cells (CD3$^+$CD4$^+$CD8$^-$CD25$^{hi}$IL-7rα$^{lo}$Foxp3$^+$Helios$^+$). Ex vivo stimulation of peripheral blood mononuclear cells (PBMCs) show MAIT cells express high levels of CTLA-4 similar to Tregs. However, unlike Tregs, CTLA-4 expression is induced uniquely on MAIT cells by inflammatory signals (IL-12, IL-15 and IL-18) even in the absence of a TCR signal (FIGS. 3A-3B). CTLA-4 expression on MAIT cells is also programmed after short term (6 hours) exposure, as the inflammatory signals do not need to be present continually for maintenance of CTLA-4 on the MAIT cell surface (FIG. 3B). Stimulation of MAIT cells with IL-12, IL-15 and IL-18 in the absence of a TCR signal induced expression of CTLA-4, and this induction was not affected by treatment of the MAIT cells with an anti-MR1 antibody (FIG. 4). Induction of CTLA-4 on MAIT cells by stimulation with IL-12, IL-15 and IL-18 in the absence of a TCR signal reduced activation of MAIT cells to 25% or less compared to a positive activated MAIT cell control, as determined by induction of CD69$^+$CD25$^+$ expression (FIG. 5E). Cytokine, cytolytic molecules, and chemokine production were reduced in MAIT cells stimulated with IL-12, IL-15 and IL-18 in the absence of a TCR signal compared to a positive activated MAIT cell control as assessed by IFNγ production (FIGS. 5B-5D), granzyme B production (FIGS. 5B and 5D), and chemokine CCL3 production (FIG. 5C). The reduction in MAIT cell activation upon stimulation with IL-12, IL-15 and IL-18 in the absence of a TCR signal was not affected by the presence or absence of an anti-MR1 antibody (FIG. 5D). The purity of the sorted CD8$^+$CD161$^{hi}$CCR6$^{hi}$CD62L$^{lo}$ MAIT cell population was confirmed by determining Vα7.2 expression (FIG. 5A).

As will be understood by one of ordinary skill in the art, each embodiment disclosed herein can comprise, consist essentially of or consist of its particular stated element, step, ingredient or component. Thus, "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the ability to induce CTLA-4 expression on the surface of a MAIT cell in the absence of a TCR signal.

Unless otherwise indicated, all numbers expressing quantities of ingredients, properties such as molecular weight, reaction conditions, and so forth used in the specification and claims are to be understood as being modified in all instances by "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"A", "an", "the", and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method comprising:

inducing expression of cytotoxic T-lymphocyte antigen 4 (CTLA-4) on mucosal-associated invariant T (MAIT) cells in the absence of a T cell receptor (TCR) signal by incubating the MAIT cells in a single culture media with an effective amount of each of interleukin (IL)-12, IL-15, IL-18, and an anti-MR1 antibody for an effective duration of time, thereby inducing the expression of the CTLA-4 on the MAIT cells in the absence of the TCR signal; and measuring the expression of the CTLA-4 on the MAIT cells after the inducing.

2. The method of claim 1, wherein the effective amount of IL-12 is 100 ng/ml, the effective amount of IL-15 is 100 ng/ml, and the effective amount of IL-18 is 100 ng/mL.

3. The method of claim 1, wherein the effective amount of the anti-MR1 antibody is 50 µg/mL.

4. The method of claim 1, wherein the effective duration of time is 24 hours.

5. The method of claim 1, wherein the effective duration of time is at least 24 hours.

6. The method of claim 1, wherein the MAIT cells are in a population of mononuclear cells.

7. The method of claim 1, wherein the MAIT cells are $CD3^+CD4^-CD8^+V\alpha7.2^+CD161^{hi}$.

8. The method of claim 1, wherein the MAIT cells are $CD8^+CD161^{hi}CCR6^{hi}CD62L^{lo}$.

9. The method of claim 1, wherein the single culture media comprises RPMI 1640 supplemented with 100 U/ml penicillin, 100 µg/ml streptomycin sulfate, and 10% FBS.

* * * * *

SEQUENCE LISTING

<160> NUMBER OF SEQ ID NOS: 10

<210> SEQ ID NO 1
<211> LENGTH: 219
<212> TYPE: PRT
<213> ORGANISM: Homo sapiens

<400> SEQUENCE: 1

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215
```

<210> SEQ ID NO 2
<211> LENGTH: 328
<212> TYPE: PRT
<213> ORGANISM: Homo sapiens

<400> SEQUENCE: 2

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
```

```
            100                 105                 110
Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
                180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 3
<211> LENGTH: 253
<212> TYPE: PRT
<213> ORGANISM: Pongo abelii

<400> SEQUENCE: 3

Met Trp Pro Pro Gly Ser Ala Ser Gln Pro Pro Ser Pro Ala Ala
1               5                   10                  15

Ala Thr Gly Leu His Pro Ala Ala Arg Pro Val Ser Leu Gln Cys Arg
                20                  25                  30

Leu Ser Met Cys Pro Ala Arg Ser Leu Leu Leu Val Ala Thr Leu Val
            35                  40                  45

Leu Leu Asp His Leu Ser Leu Ala Arg Asn Leu Pro Val Ala Thr Pro
        50                  55                  60

Gly Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Gln
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140
```

```
Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
            165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
            210                 215                 220

Thr Lys Ile Lys Leu Cys Ile Leu Leu His Ala Phe Arg Ile Arg Ala
225                 230                 235                 240

Val Thr Ile Asp Arg Val Met Asn Tyr Leu Asn Ala Ser
                245                 250

<210> SEQ ID NO 4
<211> LENGTH: 328
<212> TYPE: PRT
<213> ORGANISM: Pongo abelii

<400> SEQUENCE: 4

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Arg
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Ala
            85                  90                  95

Leu Ser His Ser Phe Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Arg Leu Pro Ile
            195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
            260                 265                 270
```

-continued

```
Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Asn Phe Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 5
<211> LENGTH: 162
<212> TYPE: PRT
<213> ORGANISM: Homo sapiens

<400> SEQUENCE: 5

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 6
<211> LENGTH: 135
<212> TYPE: PRT
<213> ORGANISM: Homo sapiens

<400> SEQUENCE: 6

Met Val Leu Gly Thr Ile Asp Leu Cys Ser Cys Phe Ser Ala Gly Leu
1               5                   10                  15

Pro Lys Thr Glu Ala Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95
```

```
Ser Asn Gly Asn Val Thr Glu Ser Gly Cys Lys Glu Cys Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser
    130                 135

<210> SEQ ID NO 7
<211> LENGTH: 162
<212> TYPE: PRT
<213> ORGANISM: Mus musculus

<400> SEQUENCE: 7

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser

<210> SEQ ID NO 8
<211> LENGTH: 193
<212> TYPE: PRT
<213> ORGANISM: Homo sapiens

<400> SEQUENCE: 8

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
```

```
            115                 120                 125
Lys Asp Thr Lys Ser Asp Ile Ile Phe Phe Gln Arg Ser Val Pro Gly
    130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 9
<211> LENGTH: 189
<212> TYPE: PRT
<213> ORGANISM: Homo sapiens

<400> SEQUENCE: 9

Met Ala Ala Glu Pro Val Glu Asp Asn Cys Ile Asn Phe Val Ala Met
1               5                   10                  15

Lys Phe Ile Asp Asn Thr Leu Tyr Phe Ile Glu Asn Leu Glu Ser Asp
                20                  25                  30

Tyr Phe Gly Lys Leu Glu Ser Lys Leu Ser Val Ile Arg Asn Leu Asn
            35                  40                  45

Asp Gln Val Leu Phe Ile Asp Gln Gly Asn Arg Pro Leu Phe Glu Asp
        50                  55                  60

Met Thr Asp Ser Asp Cys Arg Asp Asn Ala Pro Arg Thr Ile Phe Ile
65                  70                  75                  80

Ile Ser Met Tyr Lys Asp Ser Gln Pro Arg Gly Met Ala Val Thr Ile
                85                  90                  95

Ser Val Lys Cys Glu Lys Ile Ser Thr Leu Ser Cys Glu Asn Lys Ile
            100                 105                 110

Ile Ser Phe Lys Glu Met Asn Pro Pro Asp Asn Ile Lys Asp Thr Lys
        115                 120                 125

Ser Asp Ile Ile Phe Phe Gln Arg Ser Val Pro Gly His Asp Asn Lys
130                 135                 140

Met Gln Phe Glu Ser Ser Ser Tyr Glu Gly Tyr Phe Leu Ala Cys Glu
145                 150                 155                 160

Lys Glu Arg Asp Leu Phe Lys Leu Ile Leu Lys Lys Glu Asp Glu Leu
                165                 170                 175

Gly Asp Arg Ser Ile Met Phe Thr Val Gln Asn Glu Asp
            180                 185

<210> SEQ ID NO 10
<211> LENGTH: 192
<212> TYPE: PRT
<213> ORGANISM: Mus musculus

<400> SEQUENCE: 10

Met Ala Ala Met Ser Glu Asp Ser Cys Val Asn Phe Lys Glu Met Met
1               5                   10                  15

Phe Ile Asp Asn Thr Leu Tyr Phe Ile Pro Glu Glu Asn Gly Asp Leu
                20                  25                  30

Glu Ser Asp Asn Phe Gly Arg Leu His Cys Thr Thr Ala Val Ile Arg
            35                  40                  45

Asn Ile Asn Asp Gln Val Leu Phe Val Asp Lys Arg Gln Pro Val Phe
        50                  55                  60
```

```
Glu Asp Met Thr Asp Ile Asp Gln Ser Ala Ser Glu Pro Gln Thr Arg
 65              70                  75                  80

Leu Ile Ile Tyr Met Tyr Lys Asp Ser Glu Val Arg Gly Leu Ala Val
             85                  90                  95

Thr Leu Ser Val Lys Asp Ser Lys Met Ser Thr Leu Ser Cys Lys Asn
            100                 105                 110

Lys Ile Ile Ser Phe Glu Glu Met Asp Pro Pro Glu Asn Ile Asp Asp
            115                 120                 125

Ile Gln Ser Asp Leu Ile Phe Phe Gln Lys Arg Val Pro Gly His Asn
        130                 135                 140

Lys Met Glu Phe Glu Ser Ser Leu Tyr Glu Gly His Phe Leu Ala Cys
145                 150                 155                 160

Gln Lys Glu Asp Asp Ala Phe Lys Leu Ile Leu Lys Lys Lys Asp Glu
                165                 170                 175

Asn Gly Asp Lys Ser Val Met Phe Thr Leu Thr Asn Leu His Gln Ser
            180                 185                 190
```